United States Patent
Torvin et al.

(10) Patent No.: US 11,955,234 B2
(45) Date of Patent: *Apr. 9, 2024

(54) EXTRACORPOREAL BLOOD TREATMENT SYSTEM AND METHOD INCLUDING MODIFIABLE SETTINGS

(71) Applicant: GAMBRO LUNDIA AB, Lund (SE)

(72) Inventors: Bendik Torvin, Schaanwald (LI); Par-Olof Hakansson, Vellinge (SE); Maria Johnsson, Malmo (SE); AnnMargret Hakansson, Kagerod (SE); Roger Nilsson, Hoor (SE)

(73) Assignee: Gambro Lundia AB, Lund (SE)

( * ) Notice: Subject to any disclaimer, the term of this patent is extended or adjusted under 35 U.S.C. 154(b) by 43 days.

This patent is subject to a terminal disclaimer.

(21) Appl. No.: 16/309,223

(22) PCT Filed: Jun. 27, 2017

(86) PCT No.: PCT/EP2017/065762
§ 371 (c)(1),
(2) Date: Dec. 12, 2018

(87) PCT Pub. No.: WO2018/001989
PCT Pub. Date: Jan. 4, 2018

(65) Prior Publication Data
US 2019/0267138 A1    Aug. 29, 2019

(30) Foreign Application Priority Data
Jun. 30, 2016 (SE) .................................. 1650946-5

(51) Int. Cl.
*G16H 40/63*        (2018.01)
*A61M 1/14*         (2006.01)
(Continued)

(52) U.S. Cl.
CPC .............. *G16H 40/63* (2018.01); *A61M 1/14* (2013.01); *A61M 1/1601* (2014.02);
(Continued)

(58) Field of Classification Search
CPC .... A61M 1/14; A61M 1/1601; A61M 1/3621; A61M 2205/502; G06F 19/30;
(Continued)

(56) References Cited

U.S. PATENT DOCUMENTS 5,609,770 A  *  3/1997  Zimmerman ........... G06F 9/451
                                                    210/85
6,738,052 B1     5/2004  Manke
(Continued)

FOREIGN PATENT DOCUMENTS

WO       WO 98/35747      8/1998
WO       WO 2008/074316   6/2008
(Continued)

OTHER PUBLICATIONS

PCT Search Report and Written Opinion for PCT/EP2017/065762 dated Aug. 31, 2017 (14 pages).
(Continued)

*Primary Examiner* — Christopher L Gilligan
*Assistant Examiner* — Jessica Marie Webb
(74) *Attorney, Agent, or Firm* — Mueting Raasch Group

(57) ABSTRACT

Graphical user interfaces for use with extracorporeal blood treatment systems may include a plurality of mini settings cards corresponding to a plurality of settings cards. The mini settings cards may display one or more user-interactable settings, and may be selected to display the corresponding settings card. Further, each settings card may be accessed in other ways to selection of mini settings card such as, for
(Continued)

example, by selection of a process feature graphical element corresponding the settings card.

30 Claims, 13 Drawing Sheets

(51) Int. Cl.
  *A61M 1/16* (2006.01)
  *A61M 1/36* (2006.01)
  *G16H 20/17* (2018.01)

(52) U.S. Cl.
  CPC .... *A61M 1/36222* (2022.05); *A61M 1/36224* (2022.05); *A61M 1/36225* (2022.05); *G16H 20/17* (2018.01); *A61M 1/3621* (2013.01); *A61M 2205/502* (2013.01)

(58) Field of Classification Search
  CPC ........ G06F 19/3406; G06F 3/00; G06F 3/048; G06Q 50/22; G06Q 50/20–26; G16H 40/63; G16H 20/17
  USPC ............................................................. 705/2
  See application file for complete search history.

(56) References Cited

U.S. PATENT DOCUMENTS

| | | | |
|---|---|---|---|
| 9,770,554 B2 * | 9/2017 | Dollar | G09B 23/285 |
| 11,430,560 B2 * | 8/2022 | Hakansson | G06F 3/0488 |
| 2005/0045540 A1 | 3/2005 | Connell | |
| 2005/0070837 A1 | 3/2005 | Ferrarini | |
| 2005/0256444 A1 | 11/2005 | O'Mahony | |
| 2008/0249377 A1 | 10/2008 | Molducci | |
| 2008/0307353 A1 * | 12/2008 | Molducci | A61M 1/1613 715/802 |
| 2012/0029937 A1 * | 2/2012 | Neftel | A61M 1/3609 705/2 |
| 2012/0138533 A1 | 6/2012 | Curtis | |
| 2013/0190717 A1 * | 7/2013 | Dollar | A61M 1/3664 604/505 |
| 2014/0081429 A1 * | 3/2014 | Miles | G06F 3/0484 700/83 |
| 2014/0099235 A1 | 4/2014 | Ellingboe | |
| 2014/0333530 A1 | 11/2014 | Agnetta | |
| 2015/0135804 A1 * | 5/2015 | Rovatti | G01M 3/2846 73/40 |
| 2015/0227293 A1 | 8/2015 | Stenquist | |
| 2015/0238675 A1 * | 8/2015 | Carpani | A61M 1/1603 210/137 |
| 2017/0209637 A1 * | 7/2017 | Schaefer | A61M 1/367 |
| 2017/0326284 A1 * | 11/2017 | Dulsner | G16H 40/63 |

FOREIGN PATENT DOCUMENTS

| | | |
|---|---|---|
| WO | WO 2014/033119 | 3/2014 |
| WO | WO 2014/105516 | 7/2014 |
| WO | WO 2014/105517 | 7/2014 |
| WO | WO 2016/089741 | 6/2016 |
| WO | WO-2016089741 A1 * | 6/2016 ......... G06F 19/3481 |

OTHER PUBLICATIONS

PCT Search Report and Written Opinion for PCT/EP2017/065766 dated Aug. 21, 2017 (13 pages).

* cited by examiner

EXTRACORPOREAL BLOOD TREATMENT SYSTEM AND METHOD INCLUDING MODIFIABLE SETTINGS

This application is a U.S. National Stage Application of International Application No. PCT/EP2017/065762 filed 27 Jun. 2017 and published in English on 4 Jan. 2018 as International Publication No. WO 2018/001989 A1, which claims the benefit of priority under 35 U.S.C. § 119(a) of Swedish Patent Application No. 1650946-5 filed 30 Jun. 2016, each of which are incorporated herein by reference in their entireties.

The disclosure herein relates to medical treatment systems. More particularly, the disclosure relates to systems and methods for use in providing graphical user interfaces including settings cards related to medical treatment systems such as extracorporeal blood treatment systems.

Medical treatment systems often include a graphical user interface depicted on a display. A user may use the graphical user interface to, among other things, configure and setup a treatment, monitor and perform a treatment, and perform various post-treatment processes. The graphical user interface for the treatment systems may include a plurality of different graphical elements, graphical regions, and graphical areas configured for performing the functionality associated with the treatment systems.

Medical treatment systems may be configured to perform extracorporeal blood treatment using extracorporeal blood treatment apparatus. Extracorporeal blood treatment may refer to taking blood from a patient, treating the blood outside the patient, and returning the treated blood to the patient. Extracorporeal blood treatment is typically used to extract undesirable matter or molecules from the patient's blood, and/or to add beneficial matter or molecules to the blood. Extracorporeal blood treatment may be used with patients incapable of effectively eliminating such undesirable matter from their blood, for example, in the case of a patient who is suffering from temporary or permanent kidney failure. These and other patients may, for instance, undergo extracorporeal blood treatment to add to or to eliminate matter from their blood, to maintain an acid-base balance, and/or to eliminate excess body fluids.

SUMMARY

The exemplary systems and methods may be described as overcoming usability barriers and offering a user-friendly graphical user interface. For example, the graphical user interface may "open up" how blood treatments may be structured, visualized, and interacted with or operated. The exemplary systems and methods may include displaying a plurality of mini, or miniature, settings cards, each of which is selectable to display a larger settings card corresponding to the selected mini settings card. The larger settings card may include one or more settings related to, or corresponding to, one or more processes of the system or method. For example, the one or more settings may be related to an extracorporeal blood treatment and/or an extracorporeal blood treatment system. The exemplary systems and methods may be described as resulting in a unique and user-friendly way to navigate and adjust a plurality of settings and subsettings. Additionally, the display of the plurality of mini settings cards may provide user-friendly accessibility to all of a plurality of settings related to a treatment cycle. Still further, the exemplary settings cards, mini settings cards, and interaction therebetween actively contribute to the interaction between various process features and/or settings of the graphical user interface and the computing apparatus by improving the interaction between the users and the various process features and/or settings of the graphical user interface, which, in turn, improves the interaction between the various process features and/or settings of the graphical user interface and the computing apparatus. For example, the exemplary settings cards, mini settings cards, and interaction therebetween may be described as actively improving the efficiency of the interaction between the various process features and/or settings of the graphical user interface and the computing apparatus because users may be able to access such various process features and/or settings more quickly and in a more accessible manner than previous graphical user interfaces.

Current deficiencies of touch screen graphical user interfaces exist, and tendencies may exist within the field of medical treatments to make the navigation and adjustment of settings overly complex such that, e.g., the graphical user interfaces may even intimidate users/operators. For example, graphical user interfaces may be crowded with information that is badly structured and scattered with numbers and symbols. Further, for example, it may be very difficult, especially for novice users, to get a simple overview of where different settings can be found. Still further, graphical user interfaces may present too few settings at the same time, which may lead to complex navigation structures making navigation and orientation unnecessarily difficult and overwhelming.

The exemplary systems and methods may be described as providing an overview of settings or subsettings and having an intuitive navigation (e.g., being able to locate and change desired settings quickly with a sense of control and orientation and minimum effort and disorientation). Such intuitive navigation of settings and subsettings provided by the exemplary methods and systems may improve the interaction between the settings and processes of the graphical user interface and the computing apparatus because users may be able to more intuitively navigate such settings and subsettings, which in turn, will improve the interaction between such settings and subsettings and the computing apparatus. The exemplary systems and methods may use individual "cards" to present one or more user-interactable settings. Each of the individual cards may be displayed in multiple ways. For example, a plurality of mini settings cards may be displayed such that all of the settings cards including one or more settings related to, or corresponding to, a treatment cycle (e.g., preparation, treatment, and disinfection) are represented by and accessible through the displayed mini settings cards. In this way, a user may be able to see and find all of the settings of a treatment cycle through the display of the plurality of mini settings cards.

A user may also be able to access individual cards directly (e.g., without selecting a mini settings card associated therewith) by selecting, or pressing, related process feature graphical elements such as, e.g., parameter read-outs and/or settings icons on the graphical user interface. For example, data on the graphical user interface may represent shortcuts to cards in which the data or settings are located. If a user selects an ultrafiltration graphical element or segment, then an ultrafiltration settings card may be displayed (which may be the same ultrafiltration settings card that may be displayed in response to selection of an ultrafiltration mini settings card shown in the displayed plurality of mini settings cards). Further, if a user selects the "Remaining Time" number on the graphical user interface, the treatment time settings card may be displayed. This functionality may be described as creating familiarity and consistency in the settings cards and providing freedom to access the settings cards in different ways.

It may be described that the exemplary systems and methods may make navigating and handling settings easy to understand, intuitive to operate, and welcoming to users. Further, the exemplary systems and methods may be described as providing, or giving, users a clear overview of all settings, reducing stress, and improving patient safety, work flow, and efficiency. The exemplary systems and methods may translate to a better, more efficient working environment for operators, which may, thereby provide a safer and better treatment experience for patients. Additionally, the exemplary systems and methods may improve patient adherence by providing a more pleasant experience.

One exemplary extracorporeal blood treatment system may include extracorporeal blood treatment apparatus for use in performing an extracorporeal blood treatment, a display apparatus including a graphical user interface, and a computing apparatus including one or more processors and operatively coupled to the extracorporeal blood treatment apparatus and the display apparatus. The extracorporeal blood treatment apparatus may include one or more pumps, one or more sensors, and one or more disposable elements for use in performing the extracorporeal blood treatment. The graphical user interface may be configured to depict a plurality of settings cards and a plurality of mini settings cards. The computing apparatus may be configured to provide a plurality of settings cards and a plurality of mini settings cards. Each settings card of the plurality of settings cards may include one or more user-interactable settings related to one or more processes of the extracorporeal blood treatment system performable by the extracorporeal blood treatment apparatus. Each mini settings card of the plurality of mini settings cards may be associated with a different settings card of the plurality of settings cards, and each mini settings card of the plurality of mini settings cards may display at least one of the one or more user-interactable settings of the associated settings card. The computing apparatus may further be configured to display on the graphical user interface an all-settings graphical element and a plurality of process feature graphical elements. The all-settings graphical element may be associated with the display of the plurality of mini settings cards, and each process feature graphical element of the plurality of process feature graphical elements may correspond with a different process feature of the one or more processes performable by the extracorporeal blood treatment system using the extracorporeal blood treatment apparatus and may be associated with the display of a single settings card of the plurality of settings cards. The computing apparatus may further be configured to display the plurality of mini settings cards in response to a user selecting the all-settings graphical element, display a settings card of the plurality of settings cards in response to a user selecting a mini settings card of the plurality of displayed mini settings cards associated with the displayed mini settings card, and display a settings card of the plurality of settings cards in response to a user selecting a process feature graphical element of the plurality of process feature graphical elements associated with the displayed settings card. The computing apparatus may further be configured to change one or more settings related to one or more processes of the extracorporeal blood treatment system performable by the extracorporeal blood treatment apparatus in response to a user using the one or more user-interactable settings of the displayed settings card.

One exemplary method for an extracorporeal blood treatment system may include providing extracorporeal blood treatment apparatus including one or more pumps, one or more sensors, and one or more disposable elements for use in performing an extracorporeal blood treatment. The exemplary method may further include providing a plurality of settings cards and a plurality of mini settings cards. Each settings card of the plurality of settings cards may include one or more user-interactable settings related to one or more processes of the extracorporeal blood treatment system performable by the extracorporeal blood treatment apparatus. Each mini settings card of the plurality of mini settings cards may be associated with a different settings card of the plurality of settings cards, and each mini settings card of the plurality of mini settings cards may display at least one of the one or more user-interactable settings of the associated settings card. The exemplary method may further include displaying on a graphical user interface an all-settings graphical element and a plurality of process feature graphical elements. The all-settings graphical element may be associated with the display of the plurality of mini settings cards, and each process feature graphical element of the plurality of process feature graphical elements may correspond with a different process feature of the one or more processes performable by the extracorporeal blood treatment system using the extracorporeal blood treatment apparatus and may be associated with the display of a single settings card of the plurality of settings cards. The exemplary method may further include displaying the plurality of mini settings cards in response to a user selecting the all-settings graphical element, displaying a settings card of the plurality of settings cards in response to a user selecting a mini settings card of the plurality of displayed mini settings cards associated with the displayed mini settings card, and displaying a settings card of the plurality of settings cards in response to a user selecting a process feature graphical element of the plurality of process feature graphical elements associated with the displayed settings card. The exemplary method may further include changing one or more settings related to one or more processes of the extracorporeal blood treatment system performable by the extracorporeal blood treatment apparatus in response to a user using the one or more user-interactable settings of the displayed settings card.

In one or more embodiments, the one or more user-interactable settings of the plurality of settings cards may represent all of the user-interactable settings for a treatment cycle irrespective of the current phase of the treatment cycle.

One exemplary extracorporeal blood treatment system may include extracorporeal blood treatment apparatus for use in performing an extracorporeal blood treatment, a display apparatus including a graphical user interface, and a computing apparatus including one or more processors and operatively coupled to the extracorporeal blood treatment apparatus and the display apparatus. The extracorporeal blood treatment apparatus may include one or more pumps, one or more sensors, and one or more disposable elements for use in performing the extracorporeal blood treatment. The graphical user interface may be configured to depict a plurality of settings cards and a plurality of mini settings cards. The computing apparatus may be configured to provide a plurality of settings cards and a plurality of mini settings cards, and each settings card of the plurality of settings cards may include one or more user-interactable settings related to one or more processes of the extracorporeal blood treatment system performable by the extracorporeal blood treatment apparatus. The one or more user-interactable settings of the plurality of settings cards may represent all of the user-interactable settings for a treatment cycle irrespective of the current phase of the treatment cycle. Each mini settings card of the plurality of mini settings cards may be associated with a different settings card of the plurality of settings cards, and each mini settings card of the plurality of mini settings cards may display at least one of the one or more user-interactable settings of the associated settings card. The computing apparatus may further be configured to display the plurality of mini settings cards such that all of the user-interactable settings for a treatment cycle of the plurality of settings cards are accessible by a user using the plurality of mini settings cards irrespective of the current phase of the treatment cycle, display a settings card of the plurality of settings cards in response to a user selecting a mini settings card of the plurality of displayed mini settings cards associated with the displayed settings card, and change one or more settings related to one or more processes of the extracorporeal blood treatment system performable by the extracorporeal blood treatment apparatus in response to a user using the one or more user-interactable settings of the displayed settings card.

One exemplary method for an extracorporeal blood treatment system may include providing extracorporeal blood treatment apparatus including one or more pumps, one or more sensors, and one or more disposable elements for use in performing an extracorporeal blood treatment. The exemplary method may further include providing a plurality of settings cards and a plurality of mini settings cards, and each settings card of the plurality of settings cards may include one or more user-interactable settings related to one or more processes of the extracorporeal blood treatment system performable by the extracorporeal blood treatment apparatus. The one or more user-interactable settings of the plurality of settings cards may represent all of the user-interactable settings for a treatment cycle irrespective of the current phase of the treatment cycle. Each mini settings card of the plurality of mini settings cards may be associated with a different settings card of the plurality of settings cards, and each mini settings card of the plurality of mini settings cards may display at least one of the one or more user-interactable settings of the associated settings card. The exemplary method may further include displaying the plurality of mini settings cards such that all of the user-interactable settings for a treatment cycle of the plurality of settings cards are accessible by a user using the plurality of mini settings cards, displaying a settings card of the plurality of settings cards in response to a user selecting a mini settings card of the plurality of displayed mini settings cards associated with the displayed settings card, and changing one or more settings related to one or more processes of the extracorporeal blood treatment system performable by the extracorporeal blood treatment apparatus in response to a user using the one or more user-interactable settings of the displayed settings card.

In one or more embodiments, the computing apparatus may be further configured to execute or the method may further include allowing a user to select a user-interactable setting of the one or more user-interactable settings of the displayed settings card, displaying an auxiliary settings card portion including one or more additional user-interactable settings related to the selected user-interactable setting of the one or more user-interactable settings of the displayed settings card in response to the user selecting the user-interactable setting of the one or more user-interactable settings of the displayed settings card, and changing one or more settings related to one or more processes of the extracorporeal blood treatment system performable by the extracorporeal blood treatment apparatus in response to the user using the one or more additional user-interactable settings of the displayed auxiliary settings card portion.

In one or more embodiments, the plurality of settings cards may define a card set, and the plurality of settings cards may be further grouped into a plurality of card subsets. Each card subset may include a plurality of settings cards that is less settings cards than the card set, and each settings card of the plurality of settings cards and the mini settings card of the plurality of mini settings cards associated therewith may include a subset graphical indication to indicate which card subset of the plurality of card subsets the settings card and associated mini settings card belong to. In at least one embodiment, the subset graphical indication may include a color theme, and one card subset of the plurality of card subsets may be associated with blood. The subset graphical indication for the card subset associated with blood may be a red color theme. Further, one card subset of the plurality of card subsets may be associated with dialysis/dialysate fluid. The subset graphical indication for the card subset associated with dialysis/dialysate fluid may be a blue color theme. Still further, one card subset of the plurality of card subsets may be associated with general treatment settings. The subset graphical indication for the card subset associated with general treatment settings may be a green color theme.

In one or more embodiments, a plurality of user-interactable settings of the plurality of settings cards may be associated with a prescription, and the plurality of user-interactable settings of the plurality of settings cards associated with the prescription may be graphically identified in the plurality of settings cards and the mini settings cards.

In one or more embodiments, the plurality of settings cards may be associated with a treatment cycle, and the computing apparatus may be further configured to execute or the method may further include providing a plurality of system configuration settings cards defining a system configuration card set different from the plurality of settings cards associated with the treatment cycle including at least priming, treatment, and disinfection.

In one or more embodiments, when the user selects one of the plurality of displayed mini settings cards to display the associated settings card, the associated settings card may be displayed over the plurality of mini settings cards.

In one or more embodiments, when the user selects one of the plurality of process feature graphical elements to display the associated settings card, the associated settings card may be displayed without the plurality of mini settings cards being displayed. In at least one embodiment, the selected process feature graphical element may include an alphanumeric name identifying the process feature of the selected process feature graphical element and an alphanumeric value depicting the value of a parameter associated with the process feature of the selected process feature graphical element.

In one or more embodiments, the computing apparatus may be further configured to execute or the method may further include allowing a user to select an area of the graphical user interface outside of the plurality of displayed mini settings cards and removing the plurality of displayed mini settings cards from being displayed on the graphical user interface in response to the user selecting the area of the graphical user interface outside of the plurality of displayed mini settings cards.

In one or more embodiments, the computing apparatus may be further configured to execute or the method may further include allowing a user to select an area of the graphical user interface outside of the displayed settings card and removing the displayed settings card from being displayed on the graphical user interface in response to the user selecting the area of the graphical user interface outside of the displayed settings card.

In one or more embodiments, the computing apparatus may be further configured to execute or the method may further include changing one or more settings related to one or more processes of the extracorporeal blood treatment system performable by the extracorporeal blood treatment apparatus in response to a user changing the at least one of the one or more user-interactable settings on a mini settings card of the plurality of mini settings cards.

In one or more embodiments, the plurality of settings cards may include a blood settings card, an ultrafiltration settings card, a dialysis fluid settings card, and a treatment time settings card. In one or more embodiments, the plurality of settings cards may include a disinfection settings card.

In one or more embodiments, the computing apparatus may be further configured to execute or the method may further include displaying at least one settings card of the plurality of settings cards in response to a status change of one or more processes being performed. In one or more embodiments, the plurality of mini settings cards may include a plurality of persistent mini settings cards configured to always be displayed and one or more dependent mini settings cards configured to be displayed in response to at least one system configuration.

In one or more embodiments, each settings mini card of the plurality of mini settings cards may be displayed in the same location of the graphical user interface each occurrence the plurality of mini settings cards are displayed. In one or more embodiments, the display apparatus may include a touchscreen.

The above summary of the present disclosure is not intended to describe each embodiment or every implementation thereof. Advantages, together with a more complete understanding of the present disclosure, will become apparent and appreciated by referring to the following detailed description and claims taken in conjunction with the accompanying drawings.

DETAILED DESCRIPTION OF EXEMPLARY EMBODIMENTS

Figure 1:
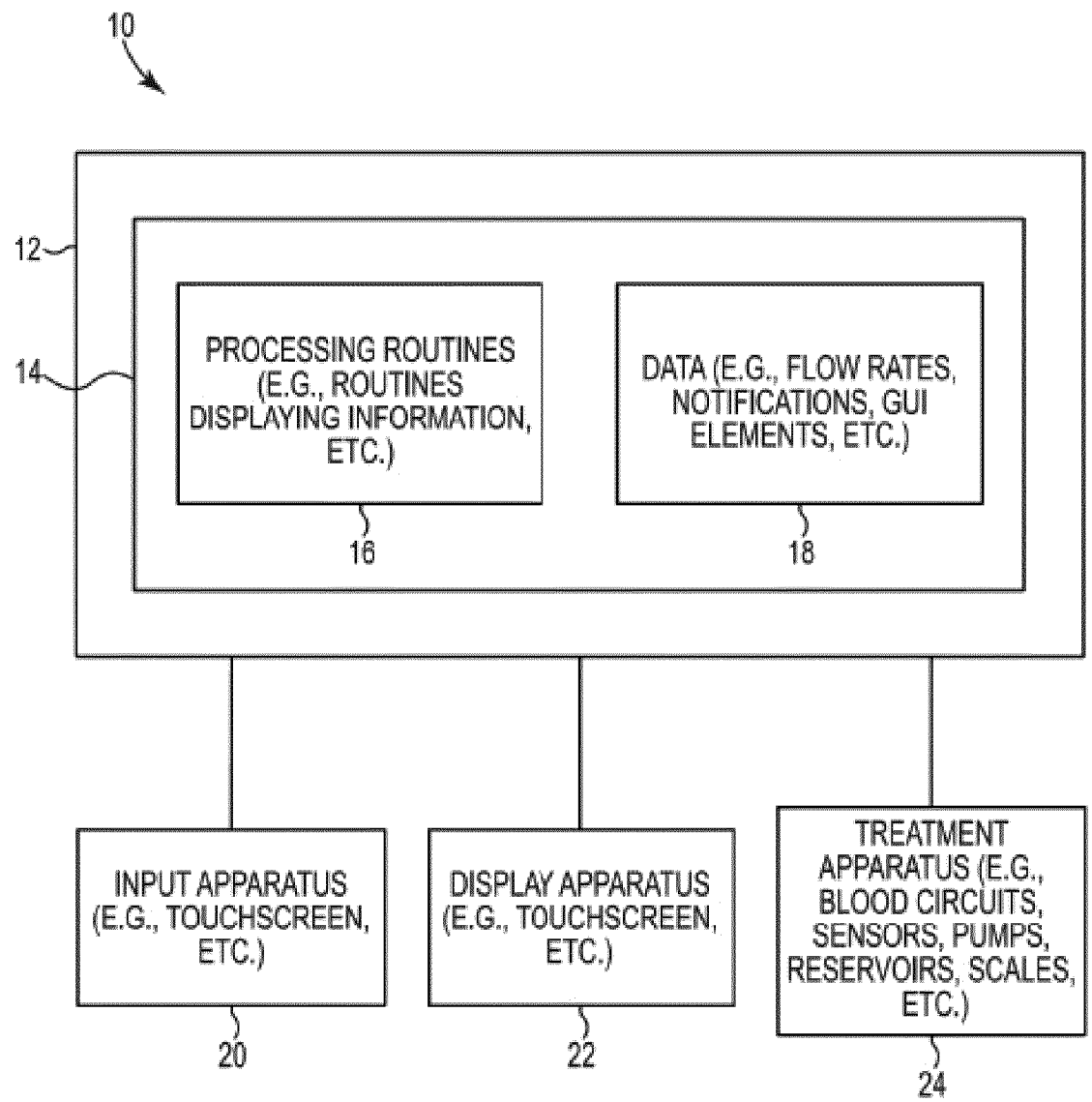
FIG. 1 is a block diagram of an exemplary medical treatment system including input apparatus, display apparatus, and treatment apparatus that may utilize the graphical user interfaces and methods described herein.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary graphical user interface systems and methods for use with medical treatment apparatus such as, e.g., extracorporeal blood treatment apparatus, shall be described with reference to FIGS. 1-12. It will be apparent to one skilled in the art that elements or processes from one embodiment may be used in combination with elements or processes of the other embodiments, and that the possible embodiments of such graphical user interface systems and methods using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

The exemplary systems and/or methods may provide, or include, graphical user interfaces (e.g., user-interactable graphical user interfaces, graphical user interfaces depicted on single-touch or multi-touch touchscreens, etc.) that include, or depict, a plurality of graphical elements, graphical regions, and graphical areas configured to allow a user to adjust one or more settings (e.g., parameters, values, modes, etc.) with respect to one or more processes (e.g., one or more processes of an extracorporeal blood treatment system, etc.). In particular, the graphical user interfaces may include a plurality of settings cards, and each settings card of the plurality of settings cards may include one or more user-interactable settings related to one or more processes of an extracorporeal blood treatment system performable by extracorporeal blood treatment apparatus.

The graphical user interfaces may further include a plurality of mini settings cards, which may be displayable in an arrangement or grid. Each of the plurality of mini settings cards may correspond to a different settings card of the plurality of settings cards, and selection of a mini settings card will display, or present, the settings card corresponding to the selected mini settings card. In other words, each mini settings card of the plurality of mini settings cards may be associated with a different settings card of the plurality of settings cards.

In one or more embodiments, all of the mini settings cards may be displayed at the same time such that users have access to all of the settings cards through selection of the mini settings cards, and as follows, access to all of the user-interactable settings provided by all of the settings cards, for a treatment cycle (e.g., preparation, treatment, and disinfection). In this way, if a user does not know where to change a particular setting, the user may initiate the display of the plurality of mini settings cards to find the particular setting. Each mini settings card of the plurality of mini settings cards may include a title describing, or representative of, the one or more settings accessible by selection thereof. Additionally, the mini settings cards may display at least one user-interactable settings of the associated settings card. In some embodiments, the mini settings cards may include, or display, all of the user-interactable settings of the associated settings card.

In at least one embodiment, all of the settings cards may be defined as being each and every settings cards as provided by the exemplary system for an exemplary treatment cycle. For example, all of the settings cards may be defined as being each and every settings card that includes settings and/or parameters related to the present treatment cycle including preparation, treatment, and post-treatment portions of the treatment cycle. Further, the settings and/or parameters of all of the settings cards may represent all of the user-interactable settings for a treatment cycle irrespective of the current phase of the treatment cycle. In other words, no matter what phase (e.g., preparation, treatment, disinfection, etc.) of a treatment cycle the system is in, all of the settings and/or parameters for the entire treatment cycle may be accessed by a user using the settings cards. Further, it may be described that all of the settings cards may not include cards that are not associated with the treatment cycle such as, e.g., service and maintenance cards, system preference cards, and/or tools cards.

The settings cards may be displayed in multiple different ways. For example, a user may initiate the display of the plurality of mini settings cards. When the plurality of mini settings cards are displayed, a user may select a mini settings card to initiate the display of the settings card corresponding to, or associated with, the selected mini settings card. Further, for example, a user may select a process feature graphical element, which may initiate the display of the settings card corresponding to, or associated with, the selected process feature graphical element. Still further, a settings cards may be automatically displayed in response to one or more events that occur during or upon the completion of one or more processes of the exemplary extracorporeal blood treatment systems and methods.

An exemplary extracorporeal blood treatment system 10 depicted in FIG. 1 may be used to execute, or perform, the exemplary graphical user interface methods and/or processes described herein. In at least one embodiment, the system 10 may be a machine for the extracorporeal treatment of blood. The system 10 could, for example, alternatively be a blood processing device or a blood component preparation device or other medical apparatus for fluid delivery/collection.

As shown, the exemplary extracorporeal blood treatment system 10 includes computing apparatus 12. The computing apparatus 12 may be configured to receive input from input apparatus 20 and transmit output to display apparatus 22.

Further, the computing apparatus 12 may include data storage 14. Data storage 14 may allow for access to processing programs or routines 16 and one or more other types of data 18 (e.g., graphical regions, graphical elements, graphical areas, graphical settings cards, graphical mini-cards, graphical stacks or decks of settings cards, graphical animations, parameters, metrics, variables, images, values, limits, text strings, macros, etc.) that may be employed to perform, or carry out, exemplary methods and/or processes (e.g., displaying graphical user interfaces, allowing user interaction with graphical user interfaces, interpreting touch gestures on a touchscreen (e.g., swipes, drags, press-and-hold, touches, presses, etc.), displaying graphical elements, displaying graphs, displaying textual elements, displaying textual values, displaying status information, issuing alarms, running a treatment, determining problems with a treatment, exchanging/changing reservoirs, notifying operators/users of problems, etc.) for use in performing extracorporeal blood treatments. The computing apparatus 12 may be operatively coupled to the input apparatus 20 and the display apparatus 22 to, e.g., transmit data to and from each of the input apparatus 20 and the display apparatus 22. For example, the computing apparatus 12 may be operatively coupled to each of the input apparatus 20 and the display apparatus 22 using, e.g., analog electrical connections, digital electrical connections, wireless connections, bus-based connections, etc. As described further herein, an operator, or user, may provide input to the input apparatus 20 to manipulate, or modify, one or more graphical elements, graphical regions, and graphical areas displayed on the display apparatus 22 to, e.g., initiate one or more actions and/or processes related to the extracorporeal blood treatment system, indicate one or more actions and/or statuses related to one or more processes of the extracorporeal blood treatment system, etc.

Further, various devices and apparatus may be operatively coupled to the computing apparatus 12 to be used with the computing apparatus 12 to perform one or more extracorporeal procedures/treatments as well as the functionality, methods, and/or logic described herein. As shown, the system 10 may include input apparatus 20, display apparatus 22, and treatment apparatus 24 operatively coupled to the computing apparatus 12 (e.g., such that the computing apparatus 12 may be configured to use information, or data, from the apparatus 20, 22, 24 and provide information, or data, to the apparatus 20, 22, 24). The input apparatus 20 may include any apparatus capable of providing input to the computing apparatus 12 to perform the functionality, methods, and/or logic described herein.

For example, the input apparatus 20 may include a touchscreen (e.g., capacitive touchscreen, a resistive touchscreen, a multi-touch touchscreen, etc.), a mouse, a keyboard, a trackball, etc. A touchscreen may be part of (e.g., overlay) the display apparatus 22 such that, e.g., an operator may use the touchscreen to interact (e.g., by touch) with a graphical user interface displayed on the display apparatus 22. For example, the input apparatus 20 may allow an operator to interact with a graphical user interface including an operation region containing, or depicting, graphical elements, graphical regions, and graphical areas associated with and representative of (or corresponding to) one or more features or processes of the extracorporeal blood treatment system when used in conjunction with the display apparatus 22 (e.g., displaying the graphical user interface). Further, more specifically, the input apparatus 20 may allow an operator to interact with a graphical user interface including a plurality of settings cards and a plurality of mini settings cards organized and displayed in a grid when used in conjunction with the display apparatus 22 (e.g., displaying the graphical user interface).

The display apparatus 22 may include any apparatus capable of displaying information to an operator, such as a graphical user interface, etc., to perform the functionality, methods, and/or logic described herein. For example, the display apparatus 22 may include a liquid crystal display, an organic light-emitting diode screen, a touchscreen, a cathode ray tube display, etc. As described further herein, the display apparatus 22 may be configured to display a graphical user interface that includes one or more graphical regions, graphical elements, and graphical areas (e.g., settings cards, settings on settings cards, etc.).

For example, the graphical user interface displayed by the display apparatus 22 may include, or display, an operation region that may include multiple graphical regions, graphical areas, and graphical elements related to the extracorporeal blood treatment system and/or for control of one or more processes during a treatment cycle (e.g., before treatment, during treatment, and after treatment). Such graphical regions, graphical areas, and graphical elements may include settings cards configured to allow a user to adjust, or configure, one or more settings associated with one or more processes of the extracorporeal blood treatment system and/or mini settings cards configured to at least display one value of the one or more settings.

As used herein, a "region" of a graphical user interface may be defined as a portion of the graphical user interface within which information may be displayed or functionality may be performed and/or controlled by a user. Regions may exist within other regions, which may be displayed separately or simultaneously. For example, smaller regions may be located within larger regions, regions may be located side-by-side, etc. Additionally, as used herein, an "area" of a graphical user interface may be defined as a portion of the graphical user interface located within a region that is smaller than the region within which the area is located. Still further, as used herein, an "element" of a graphical user interface may be defined as a component of the graphical user interface that may be located within, or adjacent to, a region, an area, or another element. In one or more embodiments, an "element" of a graphical user interface may include a perimeter, or border, defining the outer edge, or boundary, of the element. In one or more embodiments, an "element" of a graphical user interface is a defined, finite portion, item, and/or section of a graphical user interface.

The processing programs or routines 16 may include programs or routines for performing computational mathematics, touchscreen gesture interpretation algorithms, process performance algorithms, process automation algorithms, matrix mathematics, standardization algorithms, comparison algorithms, or any other processing required to implement one or more exemplary methods and/or processes described herein. Data 18 may include, for example, variables, graphics (e.g., graphical elements, graphical areas, graphical regions, settings cards, stacks of settings cards, mini settings cards, grids or arrangements of mini settings cards, portions of settings cards, auxiliary settings card portions, icons, buttons, windows, dialogs, pull-down menus, 3D graphics, images, animations, etc.), graphical user interfaces, alarm data, fluid data, flow rates, fluid volumes, notifications, pressures, pressure limits, blood flow, blood flow limits, fluid removal rates, fluid removal limits, target blood temperatures, blood temperature limits, heuristics indicative of malfunction, results from one or more processing programs or routines employed according to the disclosure herein, or any other data that may be necessary for carrying out the one and/or more processes or methods described herein.

In one or more embodiments, the system 10 may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The program used to implement the methods and/or processes described herein may be provided using any programmable language, or code, e.g., a high level procedural and/or object orientated programming language or code that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the system 10 may be implemented using a computer readable storage medium, configured with a computer program, where the storage medium so configured causes the computer to operate in a specific and predefined manner to perform functions described herein. Further, in at least one embodiment, the system 10 may be described as being implemented by logic (e.g., object code) encoded in one or more non-transitory media that includes code for execution and, when executed by one or more processors, is operable to perform operations such as the methods, processes, and/or functionality described herein.

The computing apparatus 12 may be, for example, any fixed or mobile computer system (e.g., a controller, a microcontroller, a personal computer, mini computer, etc.). The exact configuration of the computing apparatus 12 is not limiting, and essentially any device capable of providing suitable computing capabilities and control capabilities (e.g., graphics processing, control of extracorporeal blood treatment apparatus, etc.) may be used.

As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by computing apparatus 12 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by an operator.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

The methods and/or logic described in this disclosure, including those attributed to the systems, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described components may be implemented together or separately as discrete but interoperable logic devices. Depiction of different features, e.g., using block diagrams, etc., is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems, devices and methods described in this disclosure may be embodied as instructions and/or logic on a computer-readable medium such as RAM, ROM, NVRAM, EEPROM, FLASH memory, magnetic data storage media, optical data storage media, or the like. The instructions and/or logic may be executed by one or more processors to support one or more aspects of the functionality described in this disclosure.

The treatment apparatus 24 may include any apparatus used by an exemplary extracorporeal blood treatment system capable of performing extracorporeal blood treatments, such as, e.g., blood circuits, sensors, pumps, reservoirs, scales, treatment sets, filters, pressure sensors, etc. For example, the treatment apparatus 24 may include one or more elements, or components, of the extracorporeal blood treatment system 100 described herein with reference to FIG. 2.

The exemplary systems, and exemplary methods performed, or used, by such exemplary systems, described herein may include systems such as, e.g., dialysis systems. The general term "dialysis" as used herein includes hemodialysis, hemofiltration, hemodiafiltration, hemoperfusion, liver dialysis, and therapeutic plasma exchange (TPE), among other similar treatment procedures. In dialysis generally, blood is taken out of the body via an arterial blood circuit and exposed to a treatment device to separate substances therefrom and/or to add substances thereto, and is then returned to the body via a venous blood circuit. Although extracorporeal blood treatment systems capable of performing general dialysis (as defined above, including TPE) shall be described herein with reference to the exemplary extracorporeal blood treatment system of FIG. 2, other systems such as those for infusion of drugs, performance of continuous renal replacement therapy (CRRT), extracorporeal membrane oxygenation (ECMO), hemoperfusion, liver dialysis, apheresis, TPE, etc. may benefit from the systems, methods, and apparatus described herein and the present disclosure is not limited to any particular treatment system.

Figure 2:
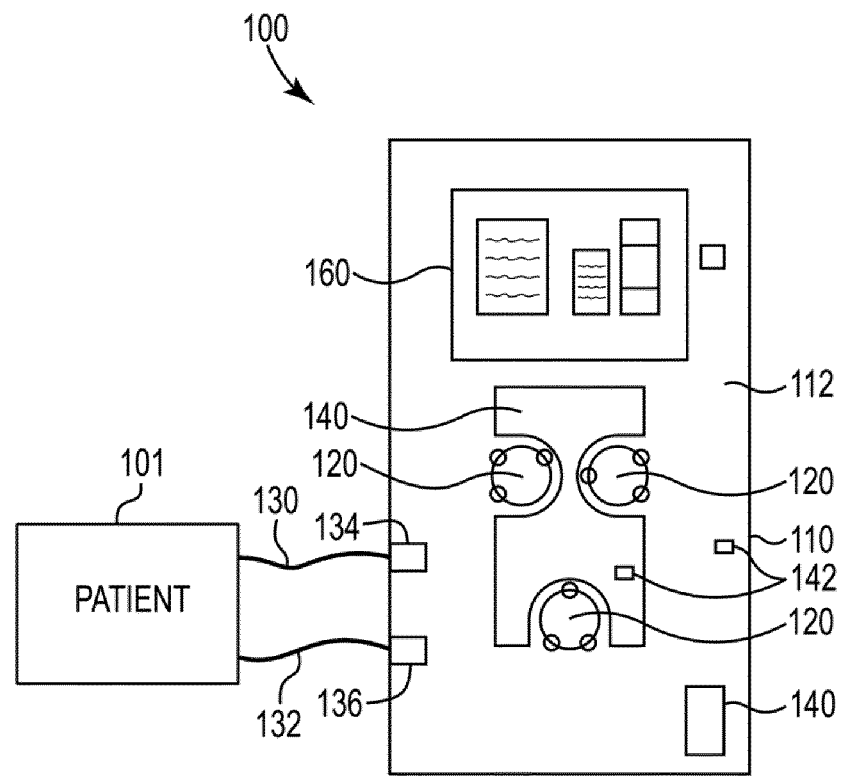
FIG. 2 is an illustration of an exemplary extracorporeal blood treatment system that may include graphical user interfaces as described herein.

Referring to FIG. 2, one illustrative embodiment of an extracorporeal blood treatment system, or apparatus, 100 is depicted. The system 100 includes a housing 110 having a front face 112. The system 100 further includes one or more pumps 120, one or more disposable elements 140 (e.g., including or part of integrated modules), and one or more sensors 142 for use in performing one or more extracorporeal blood treatments. The one or more pumps 120 may be used to move liquids through the system as part of a treatment process. Although the pumps 120 are depicted in the form of peristaltic pumps, the pumps used in the extracorporeal blood treatment system described herein may be provided in a variety of alternative forms, e.g., piston pumps, pumps for use with syringes, diaphragm pumps, etc. and/or may not be visible on the outside of the housing 110. The one or more disposable elements 140 may be coupled to the system 100 for using in performing the extracorporeal blood treatment. The one or more disposable elements 140 may include one or more fluid circuits such as, e.g., dialysis or dialysate fluid circuits, blood circuits, etc. and/or one or more blood treatment units such as, e.g., filters, etc. In at least one embodiment, a disposable element 140 is a cartridge or integrated unit including a plurality of various parts or portions configured to perform the extracorporeal blood treatment. Additionally, the one or more disposable elements 140 may include containers, or vessels, containing, or holding, one or more substances for use in the performance of the extracorporeal blood treatment. For example, a disposable element 140 may include a container, or vessel, holding bicarbonate, citrate, and/or dialysate/dialysis fluid, which may be operatively coupled to the dialysis/dialysate fluid circuit. Further, the disposable elements 140 may be described as providing at least a portion of the extracorporeal blood treatment fluid circuit that may be operatively coupled to one or more pumps 120 and one or more sensors 142 of the system 100 for use in performing extracorporeal blood treatments. As shown, two disposable elements 140 appear to be coupled to the front face 112 of the housing 110 of the system 100 to, e.g., integrate with the one or more other fluid circuits, pumps 120, and sensors 142 of the system 100.

As described herein, the one or more disposable elements 140 may be described as including one or more disposable fluid circuits and one or more blood treatment units operatively coupled to the one or more disposable fluid circuits. The one or more disposable elements 140 may be further described as including a blood circuit for receiving, circulating, and returning blood from/to a patient. The blood circuit may include one or more blood lines (e.g., as part of a disposable element). Further, the one or more disposable elements 140 may be further described as including a dialysis/dialysate circuit operatively coupled, or couplable, to the blood circuit to remove waste from the blood of the patient. The dialysis/dialysate circuit may receive, circulate, and return dialysis/dialysate fluid (e.g., returning dialysis/dialysate fluid including waste). The dialysis/dialysate circuit may include one or more dialysis/dialysate lines (e.g., as part of a disposable element 140). The blood treatment units may be, for example, a plasma filter, a hemodialysis filter, a hemofiltration filter, etc. Generally, the blood treatment units may be referred to as "filters."

As described herein, the system 100 may further include one or more sensors 142. As shown, two sensors 142 are identified on the system 100. One sensor 142 is located on, or coupled to, the front surface 112 of the housing 110 and another sensor 142 is located on the, or coupled to, the disposable elements 140. Additionally, the system 100 may include sensors 142 that are not visible on the outside of the housing 110, and instead, may be internal to the system 100 (e.g., within the housing 110). Generally, the system 100 may include any one or more sensors 142 so as to be able to monitor any value (e.g., any aspect, setting, level, condition, event internal to the system 100, etc.) of any process feature of the system 100 such as, e.g., process features during the performance of one or more extracorporeal blood treatments. For example, the system 100 may include one or more pressure sensors 142 operable to measure, or monitor, various pressures of various circuits, chambers, pods, reservoirs, etc. of the system 100, e.g., during the performance of an extracorporeal blood treatment, during the performance of a pre-treatment process, during the performance of a disinfection, post-treatment process, etc. Further, for example, the system 100 may include one or more flow rate sensors 142 operable to measure, or monitor, various fluid flow rates of fluids within various circuits, chambers, pods, reservoirs, etc. of the system 100, e.g., during the performance of an extracorporeal blood treatment, during the performance of a pre-treatment process, during the performance of a disinfection, post-treatment process, etc. Specifically, the system 100 may include one or more blood-related parameter sensors 142 such as, e.g., flow rate sensors to monitor various blood flow rates throughout the blood circuits of the system 100, blood pressure sensors to monitor the diastolic and systolic blood pressure of the patient, blood circuit pressure sensors to monitor the arterial and venous blood lines pressures, heart rate sensors to measure the patient's heart rate, etc. Further, for example, the system 100 may include one or more waste sensors 142 configured to, or operable, to measure, or monitor, an amount of waste being removing from a patient (e.g., from a patient's blood), e.g., during the performance of an extracorporeal blood treatment. Further, for example the system 100 may include one or more fluid circuit or lines sensors 142 such as, e.g., blood circuit sensors to detect whether a blood circuit is coupled or uncoupled to the system, dialysate/dialysis fluid circuit sensors to detect whether a dialysate/dialysis circuit is coupled or uncoupled to the system, etc. In other words, one or more blood circuit sensors may be configured to detect whether a blood circuit is operatively coupled to the remainder of the extracorporeal blood treatment apparatus for use in an extracorporeal blood treatment and/or one or more dialysate/dialysis fluid circuit sensors may be configured to detect whether a dialysate/dialysis circuit is operatively coupled to the remainder of the extracorporeal blood treatment apparatus for use in an extracorporeal blood treatment. In one or more embodiments, the blood circuit and dialysate/dialysis fluid circuits may include some or all of the same sensors (e.g., when the blood circuit and dialysate/dialysis fluid circuit are part of the same disposable element or cartridge). Still further, for example, the system 100 may include other sensors 142 such as fluid level sensors, temperature sensors, leak detection sensors, etc. that may be used before an extracorporeal blood treatment is performed, during the performance of an extracorporeal blood treatment, and/or after an extracorporeal blood treatment is performed.

Additionally, the extracorporeal blood treatment fluid circuit of the system 100 may be described as being completed by a combination of the disposable elements 140 and the system 100 and may be generally described as defining a blood circuit that removes blood from a patient, for example, via a catheter inserted in a vascular access of the patient, and takes the blood though a blood removal line. Then, the blood may pass through a chamber (e.g., a blood chamber) and, via a return line, may be transported back to the patient.

In one or more embodiments, the extracorporeal blood treatment system 100 may be configured for acute blood treatments (e.g., continuous renal replacement therapy) and may also include one or more devices, apparatus, and structures configured to perform the acute blood treatments. For example, the extracorporeal blood treatment system 100 may include reservoir sensors, or scales, (e.g., weight sensors, load cells, etc.), each of which is configured to hold and weigh a reservoir. The reservoir sensors may be positioned below the bottom end of the housing 110, at least in part because the reservoirs are typically attached to and hang from the reservoir sensors. The extracorporeal blood treatment systems described herein may include one or more reservoir sensors and associated reservoirs such as, e.g., as few as two reservoirs sensors and associated reservoirs, four or more reservoirs sensors and associated reservoirs, etc.

The extracorporeal blood treatment system 100 further includes a venous blood line/circuit 130 extending from a patient 101 (symbolically represented in FIG. 2) to the housing 110 to return blood to the patient 101 after the blood is treated by the system 100, an arterial blood line/circuit 132 extending from the patient 101 to the housing 110 to withdraw blood from the patient 101 for treatment, a venous blood circuit pressure sensor 134 configured to measure, or monitor, the pressure of the venous blood line/circuit 130 (e.g., the pressure of the blood, or fluid, within the venous blood line/circuit 130), and an arterial blood circuit pressure sensor 136 configured to measure, or monitor, the pressure of the arterial blood line/circuit 132 (e.g., the pressure of the blood, or fluid, within the arterial blood line/circuit 132). The venous and arterial blood circuits 130, 132 may connect the patient to a blood circuit (e.g., a disposable element 140) such that, e.g., blood of the patient may be circulated through the blood circuit to perform blood treatments thereon. In other words, the blood circuit may be connectable to a patient using the venous and arterial blood lines 130, 132.

The extracorporeal blood treatment system 100 also includes a display 160 used to show, or convey, information to an operator or user. The display 160 may also serve as an input device if, e.g., the display 160 is in the form of a touchscreen (e.g., a user interactable graphical user interface, etc.). Also, although the display 160 is depicted as being located in the housing 110, in one or more alternate embodiments, the display 160 may be separate from the housing 110 of the extracorporeal blood treatment system 100. For example, the display 160 may be movably (e.g., swivel, tilt, etc.) attached, or coupled, to the housing 110 (e.g., a top end of the housing 110).

As shown in FIG. 1 and as related to FIG. 2, the treatment apparatus 24 may be operatively coupled, or connected, to the computing apparatus 12. Among the treatment apparatus 24 operably coupled to the computing apparatus 12 may be the pumps 120, blood circuits/lines 130, 132, blood circuit pressure sensors 134, 136, and disposable elements 140 as shown in FIG. 2.

Exemplary graphical user interfaces, or portions thereof, for use in displaying information related to extracorporeal blood treatments, providing functionality to an operator for use in preparing and performing extracorporeal blood treatments (e.g., controlling performance and/or one or more processes of treatment), and/or configuring or maintaining an extracorporeal blood treatment system are depicted in FIGS. 4-12. Such exemplary graphical user interfaces may be depicted by the display apparatus 22 of the system 10 described herein with reference to FIG. 1 and/or the display 160 of the system 100 of FIG. 2. Additionally, the graphical user interfaces described herein may be depicted on a touchscreen, and in such configuration, the input apparatus would also be the touchscreen.

Each exemplary graphical user interface of the exemplary extracorporeal blood treatment systems and methods described herein may include one or more graphical elements, regions, and areas used to display information to a user. An operator may use input apparatus 20 of the exemplary extracorporeal blood treatment system 10 described herein with reference to FIG. 1 to select or manipulate graphical elements, regions, and areas of the exemplary graphical user interfaces of FIGS. 4-12. As used herein, when an operator "selects" or "interacts with" a graphical element, area, and/or region of the graphical user interface, it is to be understood that "selecting" or "interacting with" the graphical element, area, and/or region to perform one or more tasks or steps may be conducted in many different ways using many different types of input apparatus. For example, when the input apparatus includes a touch screen, an operator may select or interact with a graphical element, area, and/or region by "touching" the graphical region with their finger or using a pointing device such as a stylus. Further, for example, when the input apparatus includes a mouse or similar pointing device, an operator may select or interact with a graphical element, area, and/or region by locating an arrow or cursor over the desired graphical region "clicking" the graphical region. Still further, for example, when the input apparatus includes a series of buttons and/or knobs, an operator may select or interact with a graphical element, area, and/or region by using the buttons and/or knobs to navigate to the graphical region and to select it (e.g., by depressing the button and/or knob). Additionally, it is to be understood that selection of or interaction with a graphical element, area, and/or region may be conducted using various gestures such as, for example, but not limited to, swipes, double taps, select-and-drag, press, tracing of various shapes, pinch-inwardly, pinch-outwardly, finger spread, multi-finger touches and/or swipes, etc.

Figure 3:
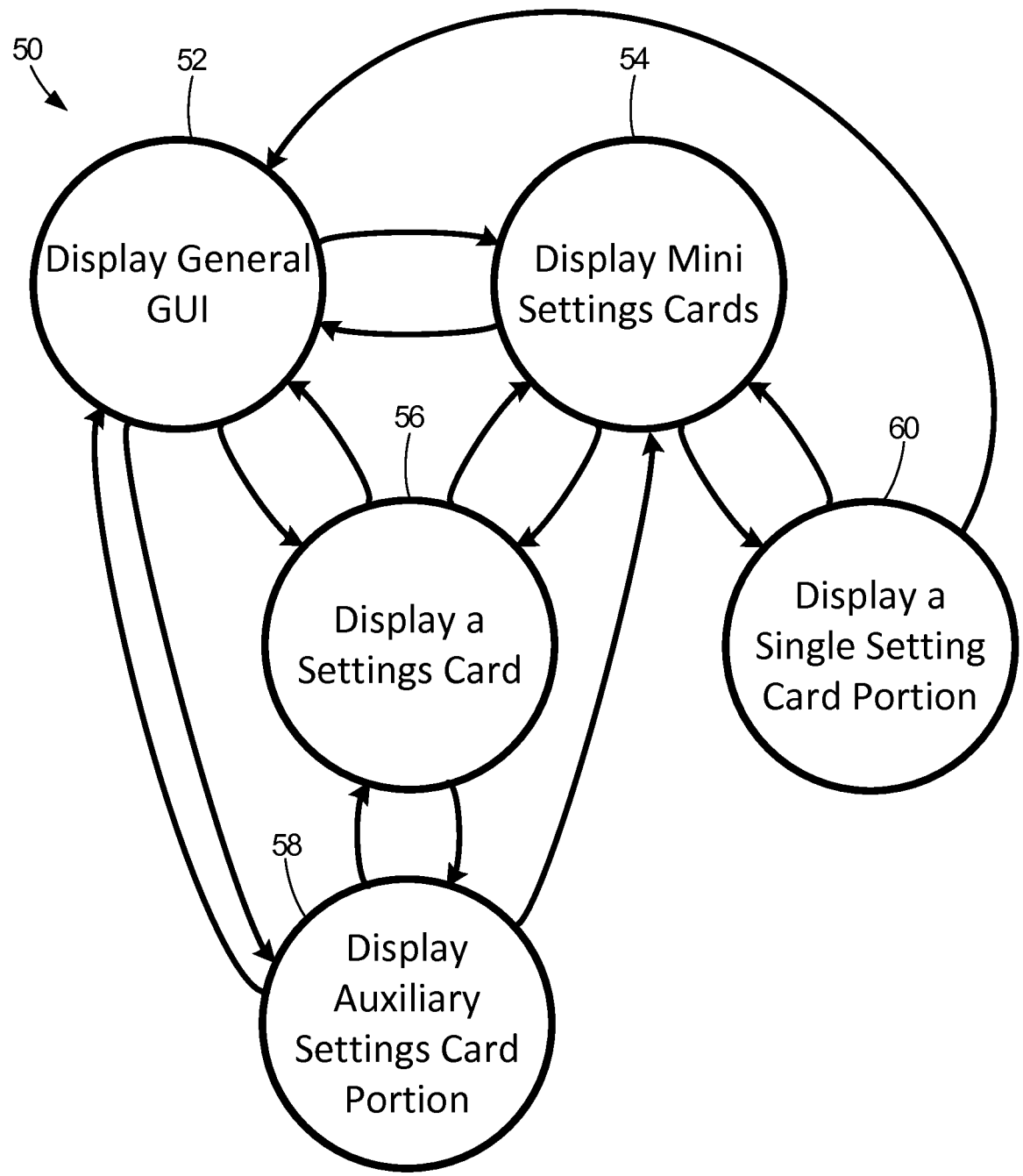
FIG. 3 is a state diagram of exemplary methods and processes for use with an exemplary graphical user interface of extracorporeal blood treatment systems such as, for example, shown generally in FIGS. 1-2.

The exemplary graphical user interface described herein with respect to FIGS. 4-12 may use, or follow, the state diagram 50 shown in FIG. 3, which will be described with respect to the graphical user interfaces shown in FIGS. 4-12. Generally, the state diagram 50 includes a general graphical user interface state 52, a mini settings cards state 54, a settings card state 56, an auxiliary settings card portion state 58, and a single settings card portion state 60.

Figure 4:
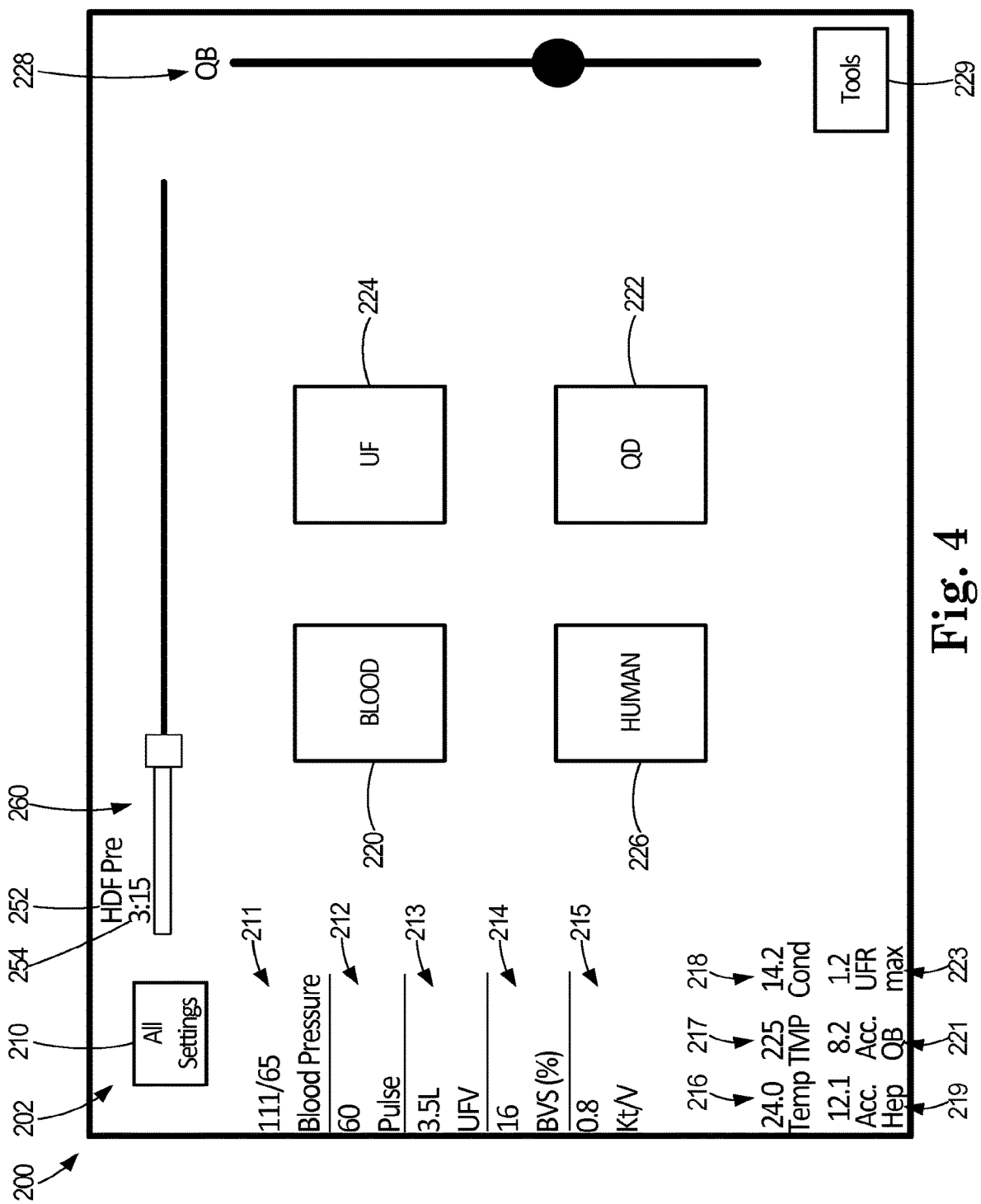
FIG. 4 depicts an exemplary graphical user interface for use with extracorporeal blood treatment systems such as, for example, shown generally in FIGS. 1-2.

An exemplary graphical user interface 200 that may correspond to the general graphical user interface state 52 of the state diagram 50 is depicted in FIG. 4. The exemplary graphical user interface 200 may be generally used to control the performance of one or more processes provided by an extracorporeal blood treatment system. As shown, the graphical user interface 200 may include a plurality of graphical regions, graphical areas, and graphical elements that may be used in the preparation or performance of an extracorporeal blood treatment as well as other functionality and/or processes of the extracorporeal blood treatment system. For example the graphical regions, graphical areas, and graphical elements may be used to indicate, initiate, revert, and stop one or more process features of one or more processes of the extracorporeal blood treatment system. The graphical elements that correspond to one or more process features may be referred to as process feature graphical elements 202, many of which are displayed in the graphical user interface 200 of FIG. 4 as will be described further herein.

Figure 5:
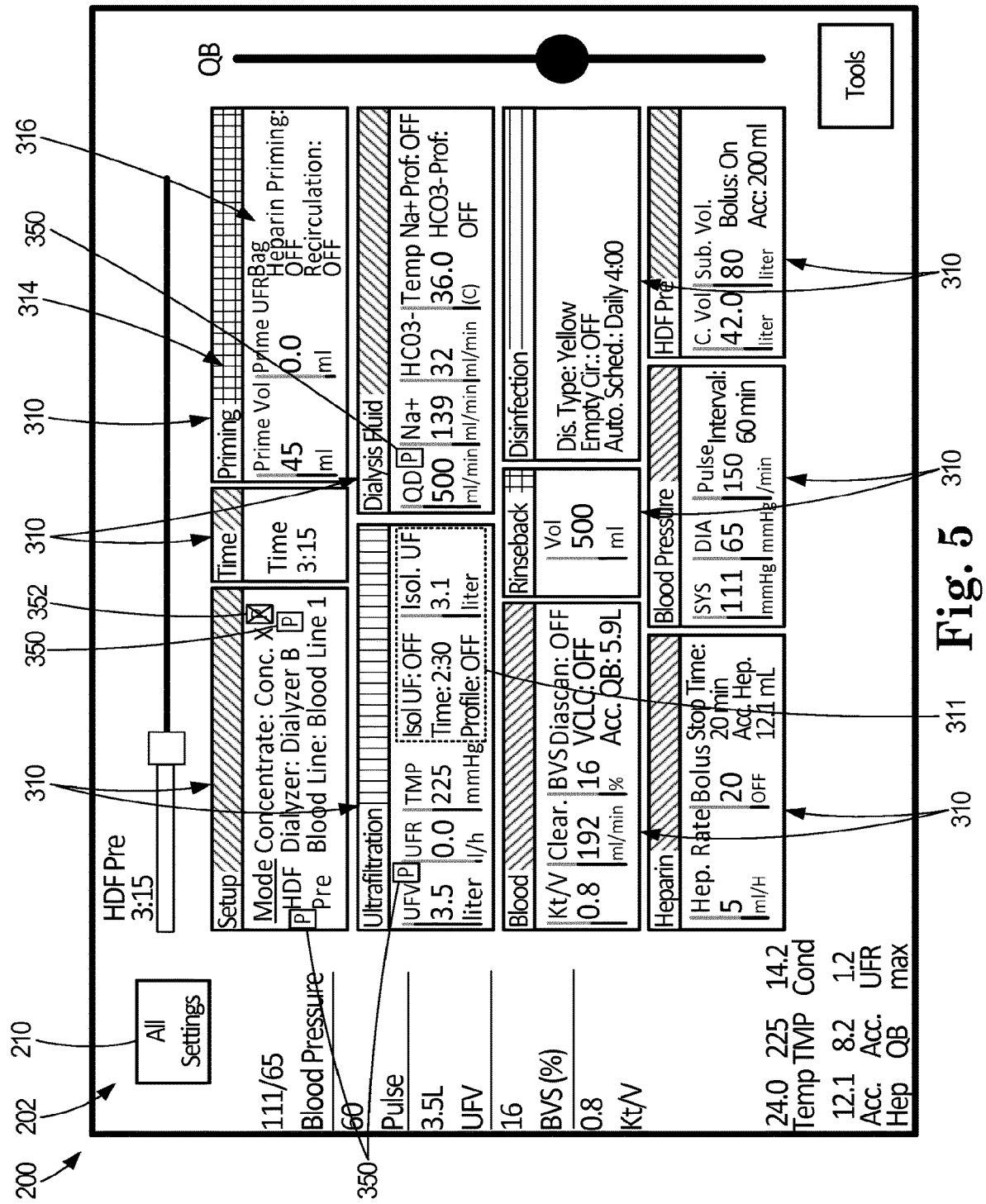
FIG. 5 depicts the graphical user interface of FIG. 4 displaying a plurality of exemplary mini settings cards.

The exemplary systems and methods described herein may include, or use, a plurality of settings cards 300 (see, e.g., FIGS. 6-9) and a plurality of mini settings cards 310 (see, e.g., FIG. 5). The settings cards and the plurality of mini settings cards may be displayed on the graphical user interface 200 to display one or more settings (e.g., values of settings, etc.) of one or more processes of the extracorporeal blood treatment system and/or related to one or more extracorporeal blood treatments performable using the extracorporeal blood treatment apparatus of the system. Further, the settings cards 300 and the mini settings cards 310 may allow a user to change the (e.g., modify, adjust, etc.) one or more settings displayed therein. For example, each of the plurality of settings cards 300 and/or mini settings cards 310 may include one or more user-interactable settings related to one or more processes of the extracorporeal blood treatment system performable by the extracorporeal blood treatment apparatus, which may be changed by a user. When such user-interactable settings are modified, or adjusted, by a user in a settings card 300 or mini settings card 310, the computing apparatus of the exemplary extracorporeal blood treatment system may change (e.g., modify, adjust, set, etc.) the user-modified, or adjusted, setting. In other words, the extracorporeal blood treatment system may make changes to a setting for a treatment in response to a user modifying, or adjusting, such a setting on a settings card 300 or mini settings card 310. The settings cards 300 and the mini settings cards 310 will be further described herein with reference to FIGS. 4-12.

In the exemplary graphical user interface 200, some of the graphical regions, graphical areas, and graphical elements such as the process feature graphical elements 202 may correspond to (e.g., representative of, associated with, etc.) an exemplary settings card 300 and/or a plurality of mini settings cards 310. For example, an all-settings graphical element 210 may correspond to a display, or used for initiation of a display, of a plurality of mini settings cards 310. For example, a user may select (e.g., touch) the all-settings graphical element 210 of FIG. 4 to change the state of the graphical user interface 200 from the general graphical user interface state 52 (such as the graphical user interface shown in FIG. 4) to the mini settings cards state 54 of the state diagram 50 of FIG. 3, which may trigger, or initiate, the display of the graphical user interface 200 of FIG. 5.

The exemplary graphical user interface 200 including the display of a plurality of mini settings cards 310 (e.g., arranged in a grid or mosaic) is shown in FIG. 5, which may have been triggered, or initiated, by the selection of the all settings graphical element 210 of FIG. 4. As shown, the plurality of mini settings cards 310 may include a "Setup" mini settings card 310, a "Time" mini settings card 310, a "Priming" mini settings card 310, a "Ultrafiltration" mini settings card 310, a "Dialysis Fluid" mini settings card 310, a "Blood" mini settings card 310, a "Rinseback" mini settings card 310, a "Disinfection" mini settings card 310, a "Heparin" mini settings card 310, a "Blood Pressure" mini settings card 310, and a "HDF Pre" mini settings card 310.

Each of the mini settings cards 310 may be persistent or dependent. A persistent, or independent, mini settings card 310 may always be displayed with the plurality of mini settings cards 310, e.g., when displayed in response to selection of the all-settings graphical element 210. For example, the "Setup" mini settings card 310, the "Time" mini settings card 310, the "Priming" mini settings card 310, the "Ultrafiltration" mini settings card 310, the "Dialysis Fluid" mini settings card 310, the "Blood" mini settings card 310, the "Rinseback" mini settings card 310, and the "Disinfection" mini settings card 310 may be persistent mini settings card 310. In other words, regardless of the treatment mode selection and the configuration of the extracorporeal blood treatment system, these persistent mini settings cards 310 are always displayed.

Conversely, mini settings cards 310 that are dependent may be displayed depending on one or more factors or settings. For example, some dependent mini settings cards 310 may only be displayed if the extracorporeal blood treatment system includes particular blood treatment apparatus. For instance, the "Heparin" mini settings card 310 may be displayed with the plurality of mini settings cards 310 if heparin delivery apparatus is included with, or part of, the blood treatment apparatus of the system. Likewise, if the heparin delivery apparatus is not included with, or part of, the blood treatment apparatus of the system, the "Heparin" mini settings card 310 may not be displayed with the plurality of mini settings cards 310. Further, the "Blood Pressure" mini settings card 310 may be displayed with the plurality of mini settings cards 310 if blood pressure measurement apparatus is included with, or part of, the blood treatment apparatus of the system. Likewise, if the blood pressure measurement apparatus is not included with, or part of, the blood treatment apparatus of the system, the "Blood Pressure" mini settings card 310 may not be displayed with the plurality of mini settings cards 310. Further, for example, some dependent mini settings cards 310 may only be displayed depending on the selected treatment mode. For instance, the "HDF Pre" mini settings card 310 may be displayed with the plurality of mini settings cards 310 if the treatment mode selected is hemodiafiltration pre-dilution, and may not be displayed if other treatment modes are selected. More specifically, treatment mode may be a user selectable item (e.g., from the "Setup" settings card 300 depicted in FIGS. 5-6), and a user may select the treatment mode to be "HDF Pre," which is hemodiafiltration pre-dilution. If HDF Pre is selected as the treatment mode, the "HDF Pre" mini settings card 310 may be displayed with the plurality of mini settings cards 310. If HDF Pre is not selected as the treatment mode, the "HDF Pre" mini settings card 310 may not be displayed with the plurality of mini settings cards 310.

Additionally, in one or more embodiments, the dependent mini settings cards 310 may be located separate from the persistent mini settings cards 310 within the graphical user interface 200 (e.g., with a separate region such as different rows). For example, as shown, the plurality of mini settings cards 310 are arranged in four rows. The uppermost three rows include the persistent mini settings cards 310 while the lowermost row includes the dependent mini settings cards 310.

Further, in one or more embodiments, the mini settings cards 310, if displayed, among the plurality of mini settings cards 310 may always be displayed, or depicted, on the graphical user interface 200 is the same location. In this way, users may become accustomed to the locations of each of the mini settings cards 310 on the graphical user interface 200, and thus, may become more efficient at navigating to the settings contained by the mini settings cards 310 and their corresponding settings cards 300. For example, all of the persistent mini settings cards 310 may always be displayed in the same locations, and, when displayed, the dependent mini settings cards 310 may also always be displayed in the same locations.

Each of the plurality of mini settings cards 310 may include a title area 314 and a settings area 316 as labeled in the "Priming" mini settings card 310. In this exemplary embodiment, the title area 314 is located proximate an upper area of the mini settings card 310 and the settings area 316 is located proximate a lower area of the mini settings card 310. In other words, a title area 314 of a mini settings card 310 may be located above a settings area 316, which includes one or more settings. In other embodiments, the title and settings areas 314, 316 may configured or arranged differently than shown in FIG. 5.

As shown in the "Priming" mini settings card 310, the title area 314 depicts the title of the mini settings card 310, which is "Priming." The title of the mini settings card 310 may describe the category of settings provided, or displayed, by the mini settings card 310, and the settings area 316 may include one or more settings of one or more processes related to the title of mini settings card 310. For example, the "Priming" mini settings cards 310 may include one or more settings in the settings area 316 related to the priming of the extracorporeal blood treatment apparatus for use prior to a blood treatment within the treatment cycle. In other words, the settings and values of settings depicted in the settings area 316 of the "Priming" mini settings card 310 may be related to one or more processes related to or associated with priming of extracorporeal blood treatment apparatus.

The one or more settings provided, or displayed, by each mini settings card 310 may include, e.g., options, values, limits, ranges, modes, profiles, time periods, time intervals, bolus values, volumes, rates, sensor values, etc. For example, the settings area 316 of the "Priming" mini settings card 310 includes priming volume (abbreviated as "Prime Vol") in milliliters depicted numerically and in a vertical bar graph, priming ultrafiltration rate (abbreviated as "Prime UFR") in milliliters depicted numerically and in a vertical bar graph, a bag heparin priming option, and a recirculation option.

In one or more embodiments, the one or more user-interactable settings depicted in the mini settings cards 310, and in turn, depicted in the settings cards 300 as further described herein may change depending on the configuration of the extracorporeal blood treatment system and the selection of treatment mode. For example, one or more user-interactable settings may not be available due to the configuration of the extracorporeal blood treatment system and/or the availability of various blood treatment apparatus as part of the system. Further, for example, one or more user-interactable settings may not be available for use in a selected treatment mode. Thus, such user-interactable settings that are not available may simply not appear, or be included within, the appropriate mini settings cards 310 and settings cards 300. In another embodiment, the user-interactable settings that are not available may be "grayed out" in the mini settings cards 310 and settings cards 300 to indicate that the user-interactable settings are not available for use. For example, one or more settings related to isolated ultrafiltration 311 such as isolated ultrafiltration: ON/OFF, isolated ultrafiltration time, isolated ultrafiltration profile, and isolated ultrafiltration volume depicted in the "Setup" mini settings card 310 may not be available depending on the configuration of the extracorporeal blood treatment system and the selection of treatment mode.

Figure 12A:
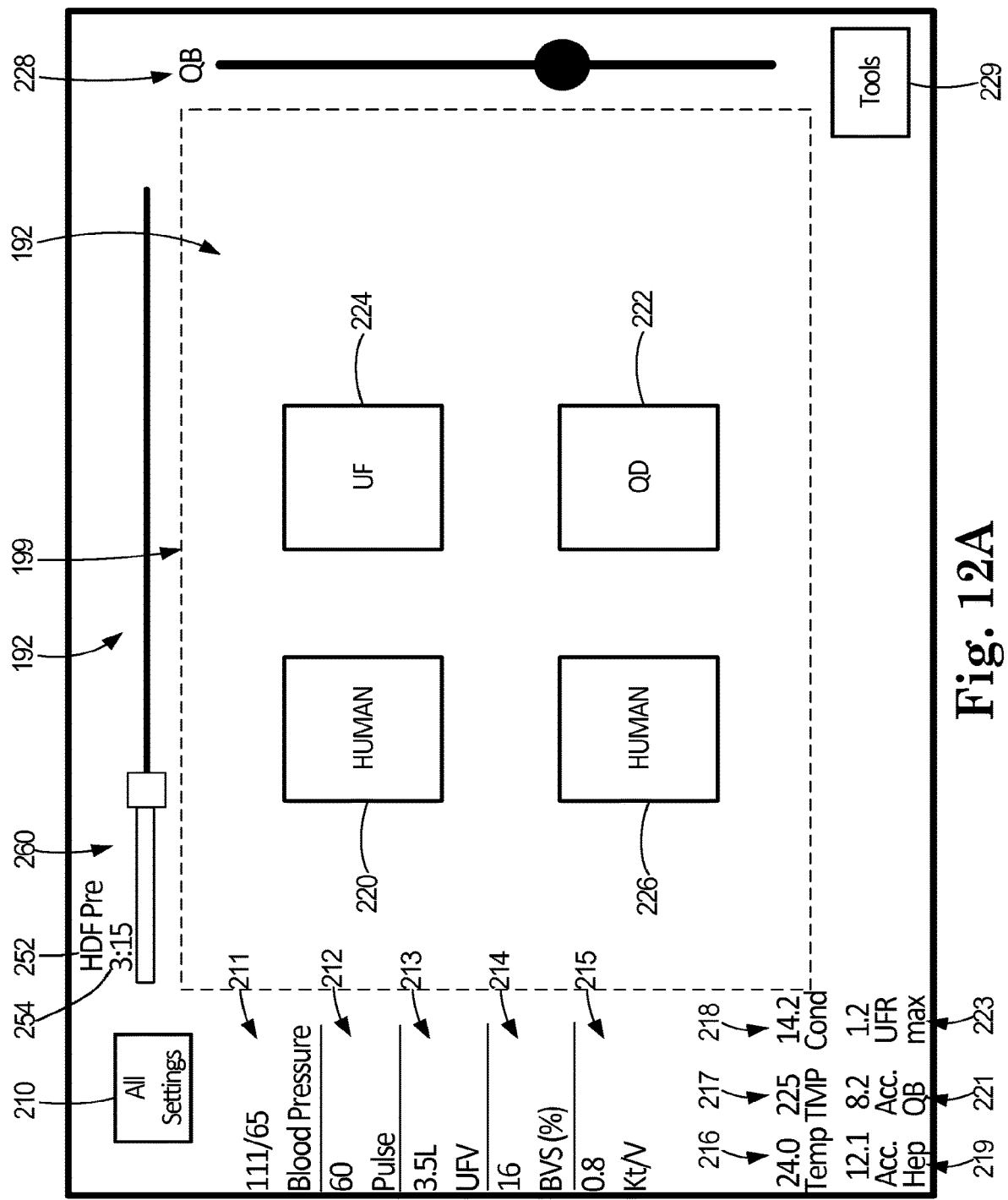
FIGS. 12A-B depict the graphical user interface of FIGS. 4-5, respectively, including a frame delineating an inside region and an outside region.
Figure 12B:
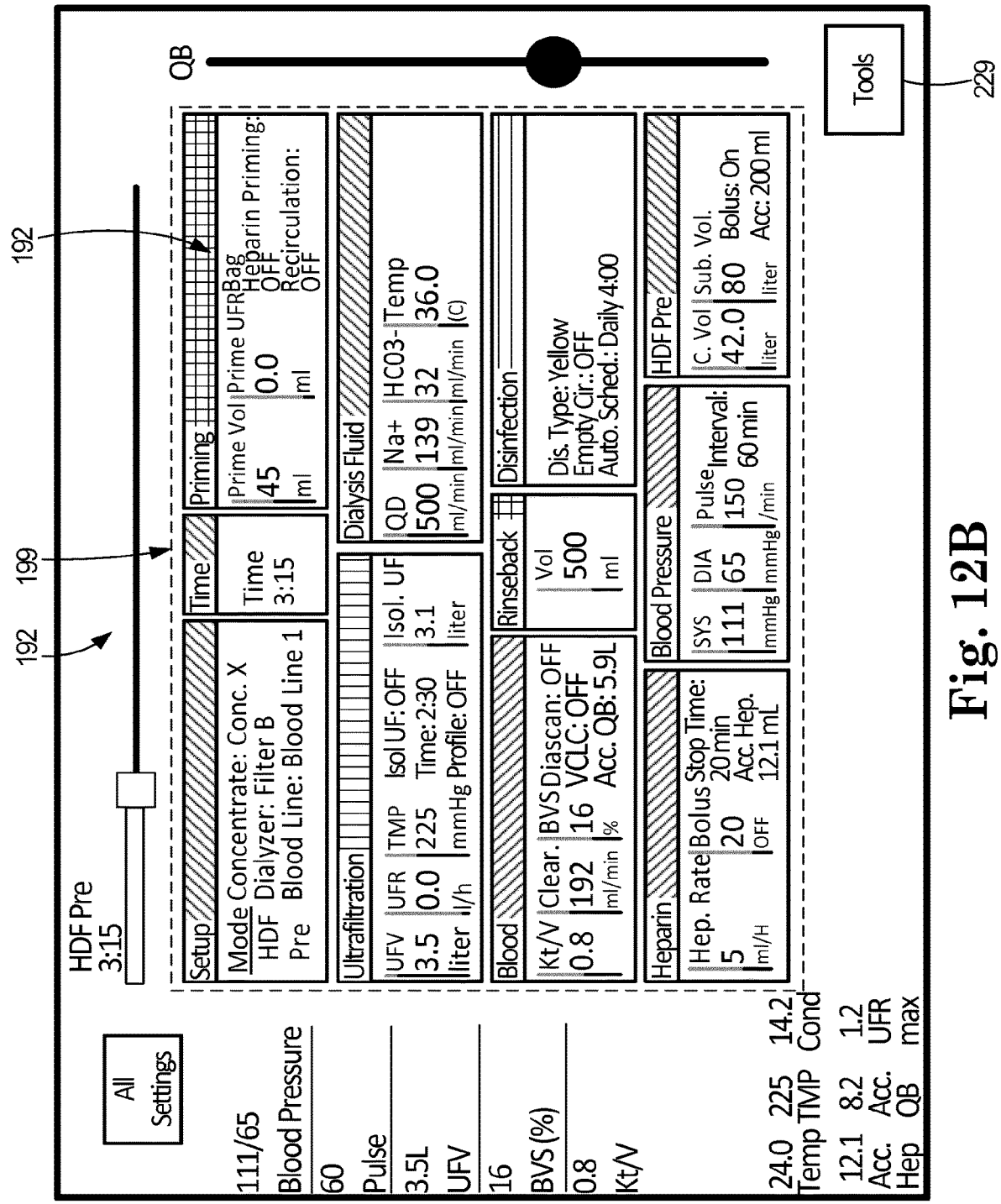

A user may return to the general graphical user interface state 52 from the mini settings cards display state 54. To return to the general graphical user interface 200 of FIG. 4, a user may select (e.g., touch) an area of the graphical user interface 200 outside of the plurality of mini settings cards 310 and not inside or proximate the process feature graphical elements 202 that, as described further herein, may display a settings card 310 directly. It may be described as shown in FIGS. 12A-12B that the plurality of mini settings cards 310 define a frame, or perimeter, 199, which will be described further herein, and if a user selects outside of the frame, or perimeter, 199 when the plurality of mini settings cards 310 are displayed, then the graphical user interface 200 will return to the general graphical user interface state 52, which is the general graphical user interface shown in FIG. 4.

The exemplary systems and methods may provide a grouping of the mini settings cards 310 and the corresponding settings cards 300 in a supportive, user intuitive way (e.g., by utilizing related settings, by utilizing how a workflow of a treatment is generally understood, etc.). Such groupings, or sets, may be indicated by a particular graphical indication such as color (shown using various crosshatching in the figures) in the title areas 304, 314 of the mini settings cards 310 and settings cards 300. For example, the "Blood" mini settings card 310, the "Heparin" mini settings card 310, and the "Blood Pressure" mini settings card 310 may be grouped together as indicated by the same crosshatching in the title area 314 as shown in FIG. 5 because, e.g., the "Blood" mini settings card 310, the "Heparin" mini settings card 310, and the "Blood Pressure" mini settings card 310 are all related to the patient's blood (e.g., obtained by monitoring the physical status of the patient). Additionally, the "Setup" mini settings card 310, the "Time" (e.g., treatment time) mini settings card 310, the "Dialysis Fluid" mini settings card 310, and the "HDF Pre" mini settings card 310 may be grouped together as indicated by the same crosshatching in the title area 314 as shown in FIG. 5. Also, in at least one embodiment, at least some mini settings cards 310 (e.g., persistent mini settings cards as described herein) and settings cards 300 may be grouped according to treatment cycle phase. For example, mini settings cards 310 and settings cards 300 primarily related to "Before Treatment" (e.g., setup and priming), "During Treatment" (e.g., prescription, medication, profiling, rinseback), and "After Treatment" (e.g., disinfection) may be grouped and identified accordingly.

Figure 6:
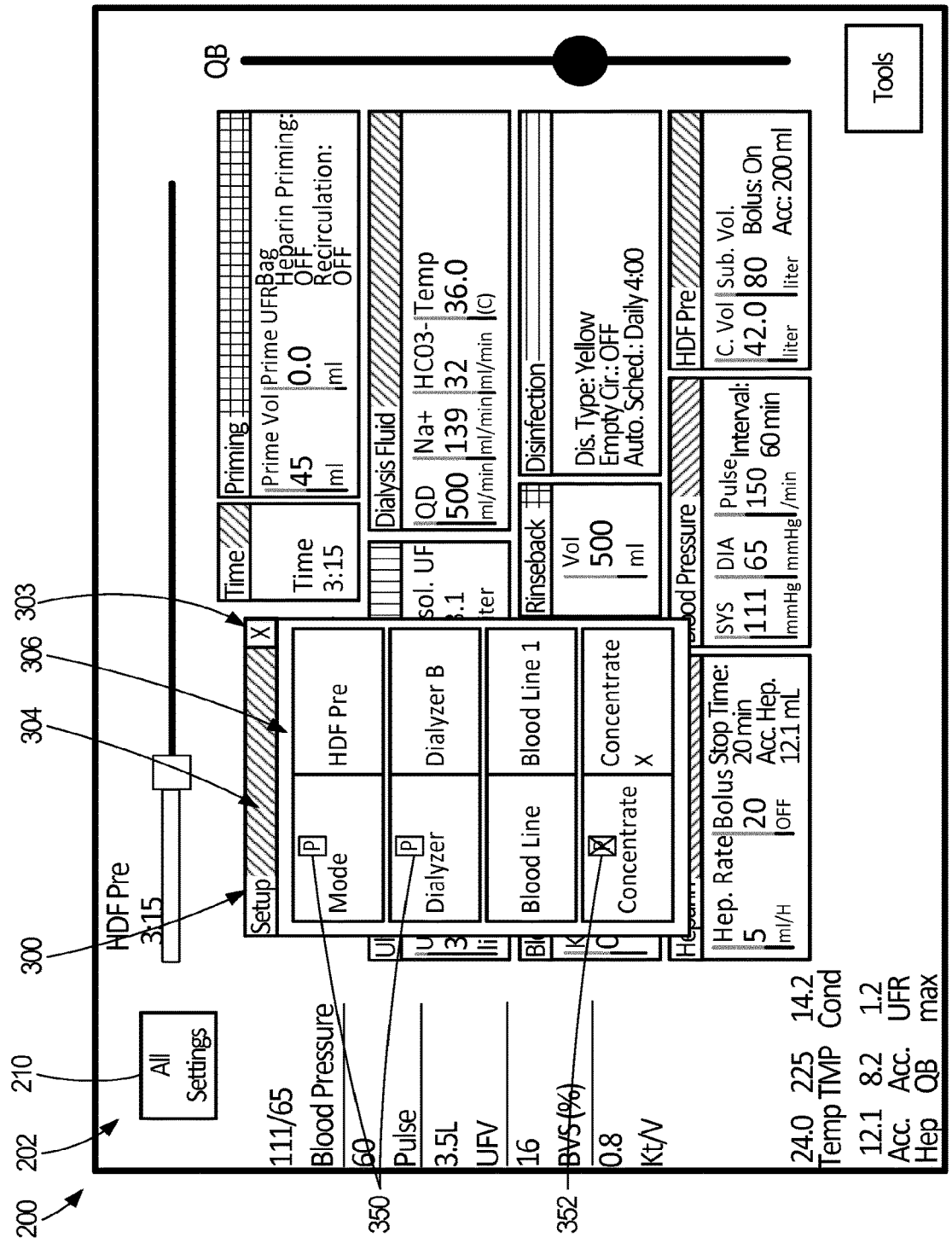
FIG. 6 depicts the graphical user interface of FIG. 5 including the plurality of mini settings cards and an exemplary "Setup" settings card.

As described herein, each of the plurality of mini settings cards 310 may correspond to or be associated with a different settings card of the plurality of settings cards 300. Likewise, each of the settings depicted in the settings area 314 of the plurality of mini settings cards 310 may correspond to or be associated with one or more user-interactable settings of the associated settings card 300. Selection of a mini settings card 310 may display, or initiate the display, of the corresponding settings card 300. For example, a user may select (e.g., touch) the "Setup" mini settings card of FIG. 5 to display the "Setup" settings card 300 as shown in FIG. 6. With respect to the state diagram 50 of FIG. 3, selection of a mini settings card 310 may change the graphical user interface 200 from the mini settings cards state 54 to the settings card state 56.

The exemplary graphical user interface 200 configured in the settings card state and including the display of the "Setup" settings card 300 is shown in FIG. 6. Similar to the mini settings cards 310, the settings cards 300 may include a title area 304 and a settings area 306 as labeled on the "Setup" settings card 300. In this exemplary embodiment, the title area 304 is located proximate an upper area of the settings card 300 and the settings area 306 is located proximate a lower area of the settings card 300. In other words, a title area 304 of a settings card 300 may be located above a settings area 306. In other embodiments, the title and settings areas 304, 306 may configured or arranged differently than shown in FIG. 6.

As shown in the "Setup" settings card 300, the title area 304 depicts the title of the settings card 300, which is "Setup." The title of the settings card 300 may describe the category of settings provided, or displayed, by the settings card 300, and the settings area 304 may include one or more user-interactable settings of one or more processes related to title of the settings card 300. For example, the "Setup" settings cards 300 may include one or more settings in the settings area 304 related to the setup of the extracorporeal blood treatment apparatus for use in a blood treatment. In other words, the settings and values of settings depicted in the settings area 304 of the "Setup" settings card 300 may be related to one or more processes related to or associated with setup of extracorporeal blood treatment apparatus.

As shown, the settings area 306 of the "Setup" settings card 300 includes a treatment mode setting for selection of the type, or mode, of treatment, a dialyzer setting for selection of the dialyzer used in a treatment, a blood line setting for selection of the type of blood line and either single or double needle access to be used in a treatment, and a concentrate setting for selection of a type of concentrate to be used in a treatment. In this example, the selected treatment mode is "HDF Pre," the selected dialyzer is the "Dialyzer B," the selected blood line is "Blood Line 1," the selected Concentrate is "Concentrate X."

Additionally, similar to as before, if a user desires to return to the general graphical user interface 200 of FIG. 4 without the display of the settings card 300 or the plurality of mini settings cards 310, a user may select (e.g., touch) an area of the graphical user interface 200 outside of both of the plurality of mini settings cards 310 and the displayed "Setup" settings card 300 and not within a process feature graphical element 202. With respect to the state diagram of FIG. 3, selection of an area outside of both the plurality of mini settings cards 310 and the displayed "Setup" settings card 300 and not within a process feature graphical element 202 will change the graphical user interface 200 from the settings card state 56 to the general graphical user interface state 52.

Further, a user may desire to return to the plurality of mini settings cards 310 being displayed without a settings card 300 being displayed as shown in FIG. 5. To do so, a user may select an area of the graphical user interface 200 outside of the settings card 300 but inside the area defined by the plurality of mini settings cards 310, may be select a close graphical element 303 of the settings card 300, or may select the all-settings graphical element 210. With respect to the state diagram of FIG. 3, selection of an area of the graphical user interface 200 outside of the settings card 300 but inside the area defined by the plurality of mini settings cards 310, selection of the close graphical element 303, or selection of the all-settings graphical element 210 may change the graphical user interface 200 from the settings card state 56 to the mini settings card state 54.

Figure 7:
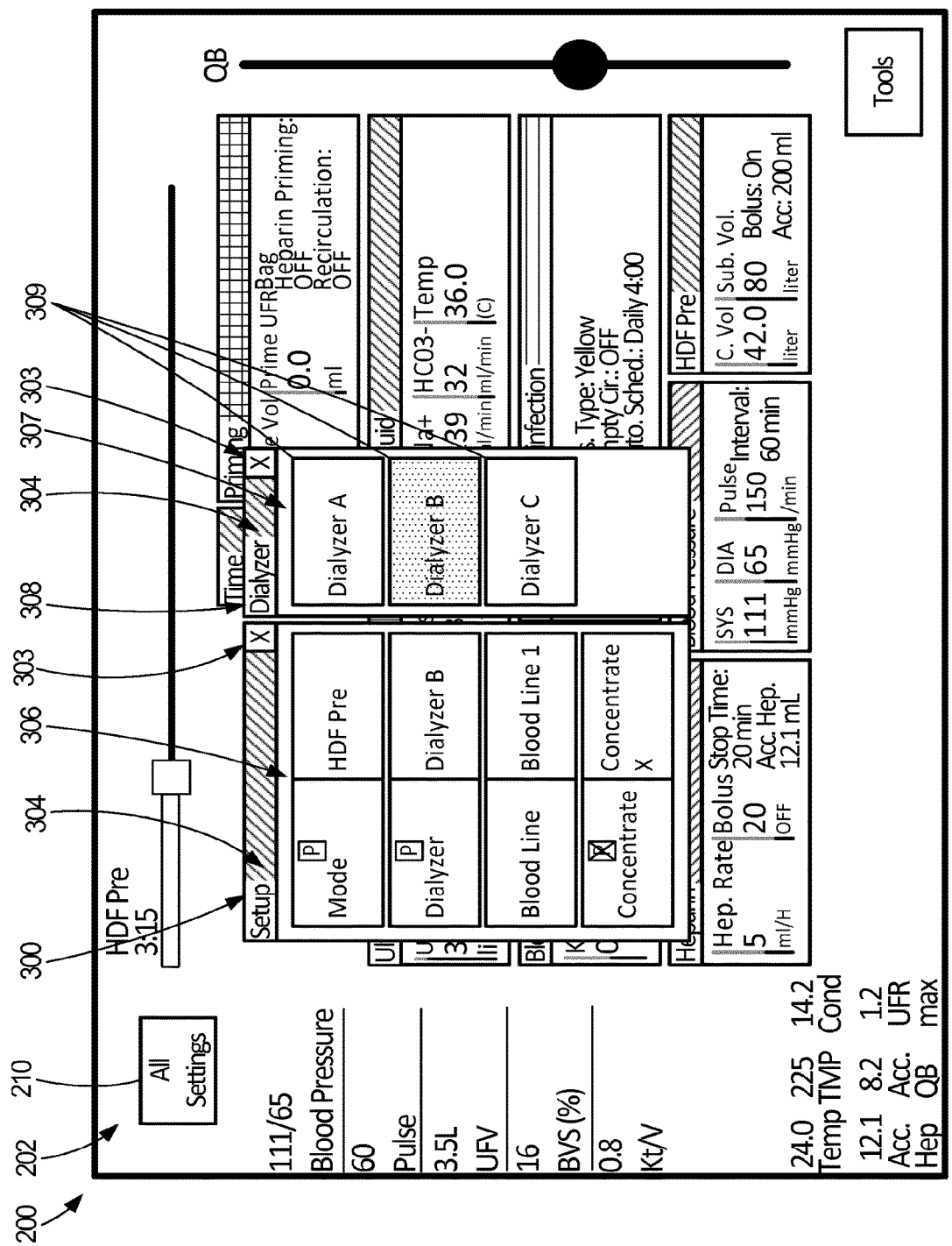
FIG. 7 depicts the graphical user interface of FIG. 6 including the "Setup" settings card and an exemplary auxiliary settings card portion corresponding to the "Setup" settings card.
Figure 8:
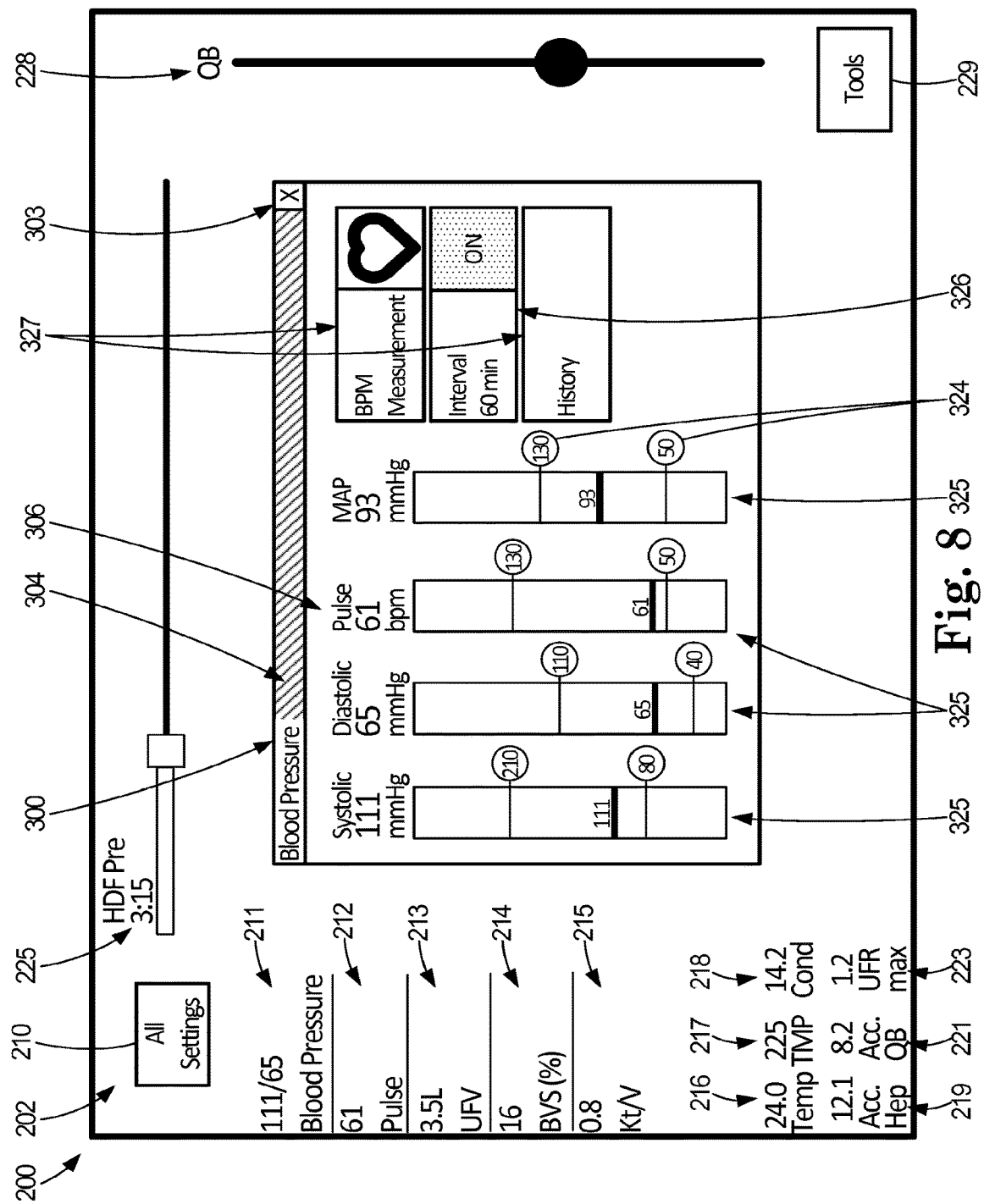
FIG. 8 depicts the graphical user interface of FIG. 5 including the plurality of mini settings cards and an exemplary "Blood Pressure" settings card.
Figure 9:
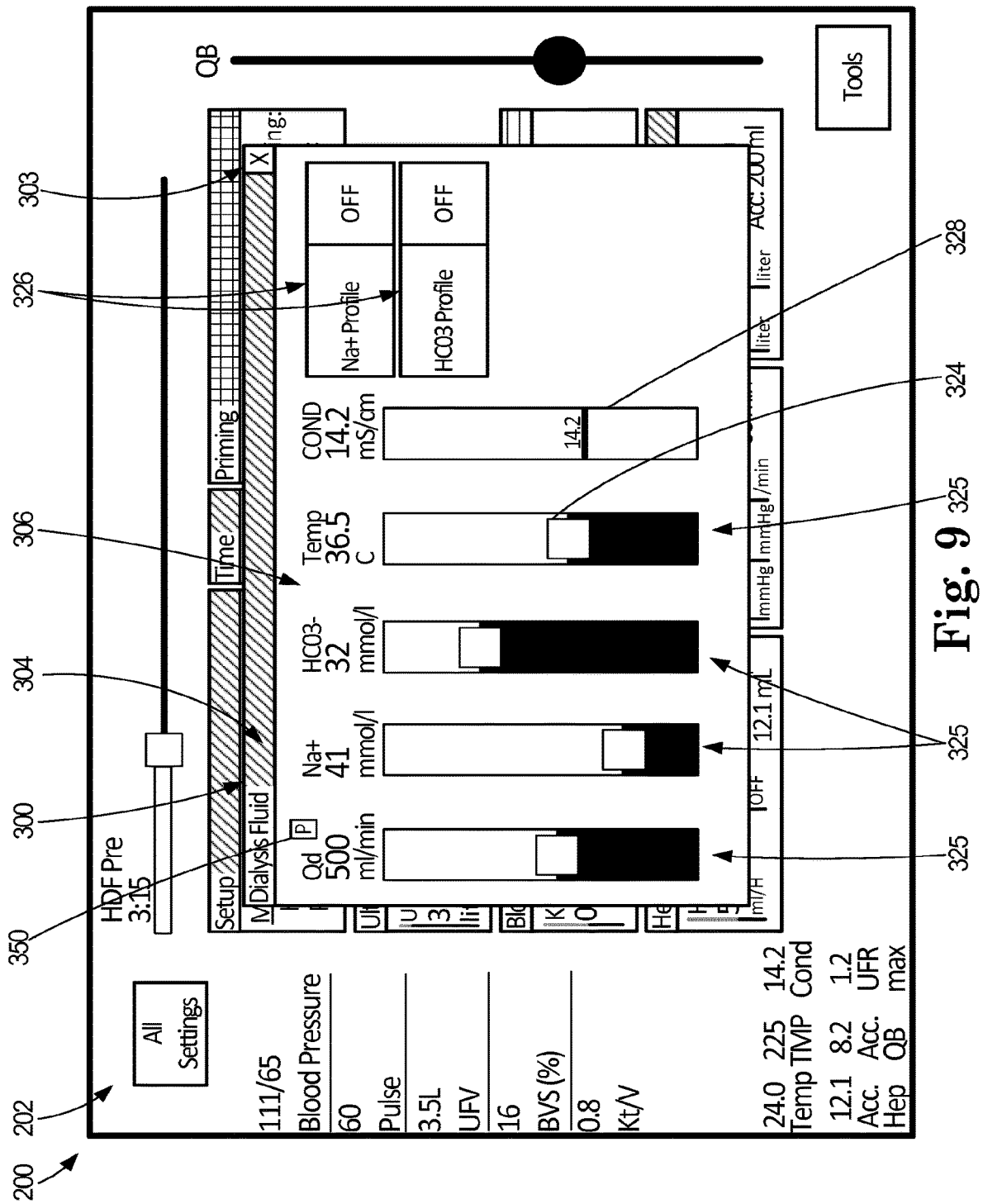
FIG. 9 depicts the graphical user interface of FIG. 5 including the plurality of mini settings cards and an exemplary "Dialysis Fluid" settings card.

While a settings card 300 is displayed, a user may select one of the user-interactable settings of the settings area 306 of the settings card 300 to change (e.g., modify, adjust, etc.) the selected user-interactable setting. The one or more user-interactable settings may often be more than one setting, and thus, be described as a plurality of settings. The settings may include a plurality of different types of settings elements such as, e.g., on/off switch elements such as shown in FIGS. 8-9, item selection elements such as shown in FIG. 7, and bar-type parameter adjustment elements such as shown in FIGS. 8-9.

In some other exemplary embodiments, an additional graphical element may be displayed in response to a user selecting a user-interactable setting within the settings card 300. For example, a user may select (e.g., touch) the dialyzer user-interactable setting of the settings area 306 of the "Setup" settings card 300 of FIG. 6 to change the type of dialyzer (e.g., a disposable element 140) to be used in a treatment. In response to the selection of the dialyzer user-interactable setting ("Dialyzer") of the settings area 306, an auxiliary settings card portion 308 may be displayed as shown in FIG. 7. With respect to the state diagram 50 of FIG. 3, selection of the dialyzer user-interactable setting ("Dialyzer") of the "Setup" settings card 300 will change the graphical user interface 200 from the settings card state 56 to the auxiliary settings card portion state 58.

The auxiliary settings card portion 308 may be described as an extension of the settings card 300 that the auxiliary settings card portion 308 is associated with and may be depicted in proximity to the associated settings card 300. For example, the auxiliary settings card portion 308 shown in FIG. 7 may be described as an extension to the "Setup" settings card 300 and may be displayed to the right side of the "Setup" settings card 300. In this example, the auxiliary settings card portion 308 includes a title area 304 ("Dialyzer") and a setting selection area 307 including three options for the dialyzer: "Dialyzer A," "Dialyzer B," or "Dialyzer C." As shown, the "Dialyzer B" is highlighted (e.g., stippled) indicating that it is presently selected. A user may select a different dialyzer such as the "Dialyzer A" or "Dialyzer C" by selection of an item graphical selection element 309 (e.g., button corresponding thereto). In other words, the auxiliary settings card portion 308 may be described including item graphical selection elements 309 configured to allow a user to select an item from a list, or group, of items, which in this example are "Dialyzer A," "Dialyzer B," or "Dialyzer C.

Selection of a graphical element 309 associated within a dialyzer may remove the auxiliary settings card portion 308 and return the graphical user interface 200 back to as shown in FIG. 6. Further, if a user is satisfied with the selected dialyzer and wishes to return to the "Setup" settings card 300, the user may select a close graphical element 303 of the auxiliary settings card portion 308. With respect to the state diagram 50 of FIG. 3, selection of a graphical element 309 associated within a dialyzer or the close graphical element 303 may change the graphical user interface 200 from the auxiliary settings card portion state 58 to the settings card state 56.

Additionally, if a user decides to return to the mini settings cards state 54, the user may select an area of the graphical user interface outside of the settings card 300 and auxiliary settings card portion 308 but inside the area defined by the plurality of mini settings cards 310, which will return the graphical user interface 200 to as shown in FIG. 5. Still further, if a user decides to return to the display of general graphical user interface 52, the user may select an area of the graphical user interface outside of the settings card 300, auxiliary settings card portion 308, and outside of the plurality of mini settings cards 310, which will return the graphical user interface 200 to as shown in FIG. 4.

One or more user-interactable settings of the settings cards 300 and the mini settings cards 310 may be associated with a prescription. For example, one or more user-interactable settings of the settings cards 300 and the mini settings cards 310 may be set by a prescription entered in the treatment system (e.g., over a network, from a memory stick, by a user, etc.). When user-interactable settings are set by a prescription, the user-interactable settings may be graphically identified in the settings cards 300 and mini settings cards 310 as being part of the prescription. For example, prescription-set user-interactable settings may be graphically highlighted using underling, italicizing, various colors, the use of graphical identifiers, icons (e.g., download icons), etc. In the embodiment depicted herein, a prescription graphical element 350 is depicted proximate each of the user-interactable settings that are set via a prescription within the mini settings cards 310 as shown in FIG. 5 and the settings cards 300 as shown in FIGS. 5-9. As shown, the prescription graphical element 350 is a rectangle including the letter "P" within the rectangle. Additionally, after a user modifies a prescription-set user-interactable setting, the prescription graphical element 350 may change to a modified prescription graphical element 352 to indicate that the value of the prescription-set setting has been changed or modified. For example, as shown in FIG. 5, the treatment mode, "HDF Pre," "Concentrate," and "Dialyzer" of the "Setup" mini settings card 310 and corresponding settings card 300 have been set via prescription. However, a user has changed the "Concentrate" from the prescription set concentrate value to "Conc. X," and as such, the prescription graphical element 350 has been changed to a modified prescription graphical element 352 to indicate that the prescription-set concentrate has been changed or modified from the prescription. Thus, the prescription graphical element 350 and the modified prescription graphical element 352 may provide users a convenient way to determine whether a prescription has been used, and if so, what settings have been modified from the prescription.

As described herein, some of the graphical regions, graphical areas, and graphical elements may correspond to (e.g., representative of, associated with, etc.) process features of the one or more processes performable by the extracorporeal blood treatment system. Further, some of the graphical regions, graphical areas, and graphical elements may be interactable (e.g., movable, portions movable, etc.) to initiate, control, and/or perform one or more processes performable by the extracorporeal blood treatment system while other graphical regions, graphical areas, and graphical elements may be stationary and display information related to one or more processes performable by the extracorporeal blood treatment system. Regardless of the ability to be interactable, many graphical regions, graphical areas, and graphical elements may be selectable to display settings cards 300 associated therewith as described further herein.

Exemplary interactable process feature graphical elements shown in FIG. 4 may include a blood process feature graphical element 220, a dialysis fluid process feature graphical element 222, an ultrafiltration process feature graphical element 224, a human process feature graphical element 226, and a blood flow process feature graphical element 228, each of which may correspond to one or more processes performable by the extracorporeal blood treatment system. Further, each of the blood process feature graphical element 220, the dialysis fluid process feature graphical element 222, the ultrafiltration process feature graphical element 224, and the human process feature graphical element 226 may be movable with respect to each other to control or perform one or more processes of the extracorporeal blood treatment system. Further, portions of the blood flow process feature graphical element 228 may be used to adjust the blood flow rate of a treatment. Additionally, exemplary stationary process feature graphical elements shown in FIG. 4 may include a blood pressure process feature graphical element 211, a patient pulse process feature graphical element 212, a ultrafiltration volume process feature graphical element 213, a blood volume sensor process feature graphical element 214, Kt/V process feature graphical element 215, a temperature process feature graphical element 216, a transmembrane pressure process feature graphical element 217, a conductivity process feature graphical element 218, an accumulated heparin process feature graphical element 219, an accumulated blood flow rate 221, a maximum ultrafiltration rate process feature graphical element 223, a treatment mode identifier process feature graphical element 252, a treatment time process feature graphical element 254, and a treatment timeline process feature graphical element 260 may be displayed on the graphical user interface 200, each of which may also correspond to one or more processes performable by the extracorporeal blood treatment system.

Selection of a process feature graphical element 202, such as the specific process feature graphical elements labeled with respect to FIG. 4, may display a single settings card 300 related to the selected process feature graphical element 202. For example, a "Blood Pressure" settings card 300 may be displayed in response as shown in FIG. 8 to a user selecting the blood pressure process feature graphical element 211. With respect to the state diagram of FIG. 3, the graphical user interface may be changed from the general graphical user interface state 52 to the display a settings card state 56 in response to selection of a process feature graphical element 202 such as the blood pressure process feature graphical element 211. Further shown in FIG. 8, the "Blood Pressure" settings card 300 is not displayed over the plurality of mini settings cards 310 in response to selection of the blood pressure process feature graphical element 211, and as such, selection outside of the settings card 300 or selection of the close graphical element 303 may return the graphical user interface 200 back to the general graphical user interface 200 of FIG. 4 (e.g., the general graphical user interface state 52 as opposed to the mini settings card state 54).

The "Blood Pressure" settings card 300 may include a plurality of bar-type parameter adjustment elements 325, a switch element 326, and two selection elements 327. The bar-type parameter adjustment elements 325 may allow users to visualize a numerical value of a process feature and may be used by the users to adjust one or more numerical parameters related to the process feature using handle element 324, which may be movable along the bar-type adjustment element 325. As shown, the patient's systolic blood pressure is 111 millimeters of Mercury (mmHg) as depicted numerically and within the bar-type adjustment element 325. Additionally, alarm limits regarding the patient's systolic blood pressure are indicated by lines within the bar-type adjustment element 325. A user may use the bar-type parameter adjustment elements 325 to adjust each of these alarm values. For example, a user may select the handle element 324 and move the handle element 324 upwardly or downwardly along the bar-type parameter adjustment element 325 to adjust the numerical parameters associated therewith. As shown, the alarm limits are set at 210 mmHG and 80 mmHG for the patient's systolic blood pressure. Additional bar-type adjustment elements 325 are depicted in the "Blood Pressure" settings card 300 for the patient's diastolic blood pressure, pulse, and mean arterial pressure (MAP).

The selection elements 327 in the "Blood Pressure" settings card 300 include a blood pressure measurement (BPM) selection element 327 and a history selection element 327. Selection of the blood pressure measurement (BPM) selection element 327 may initiate a blood pressure measurement and selection of the history selection element 327 may display a blood pressure history interface including recorded blood pressure data for a treatment cycle.

As shown, the switch element 326 in the "Blood Pressure" settings card 300 indicates the interval for blood pressure measurement is 60 minutes and is "ON." A user may select the switch element 326 to switch, or change the 60 minute interval for blood pressure measurement to be "OFF." Generally, switch elements may be configured to allow a user to select whether a particular process feature is "on" or "off" (e.g., "true" or "untrue," "used" or "unused," etc.).

A "Dialysis Fluid" settings card 300 is depicted over the plurality of mini settings cards 310 in FIG. 9. To the display the "Dialysis Fluid" settings card 300, a user may have selected the "Dialysis Fluid" mini settings card 310 from the display of the plurality of mini settings cards 310 depicted in FIG. 5 or the dialysis fluid process feature graphical element 222 depicted in FIG. 4. As shown, the "Dialysis Fluid" settings card 300 includes four bar-type parameter adjustment elements 325, one bar-type parameter display element 328, and two switch elements 326. The four bar-type parameter adjustment elements 325 may correspond to and display values with respect to dialysate/dialysis fluid flow rate, dialysate/dialysis fluid sodium concentration, dialysate/dialysis fluid bicarbonate concentration, and dialysate/dialysis fluid temperature, each of which may be adjusted by a user selecting and moving the handle element 324 along the bar element. The bar-type parameter display element 328 may correspond to and a display value with respect to the dialysate/dialysis fluid conductivity. The bar-type parameter display element 328 may not allow adjustment of the values/settings associated therewith, and instead, may only be for display purposes. The two switch elements 326 include a sodium (Na+) profile switch element 326 to initiate ("ON") or disable ("OFF") a sodium profile process feature and a bicarbonate (HCO3−) profile switch element 326 to initiate ("ON") or disable ("OFF") a bicarbonate profile process feature. As shown, each of the sodium profile switch element 326 and the bicarbonate profile switch element 326 are switched to "OFF."

Figure 10:
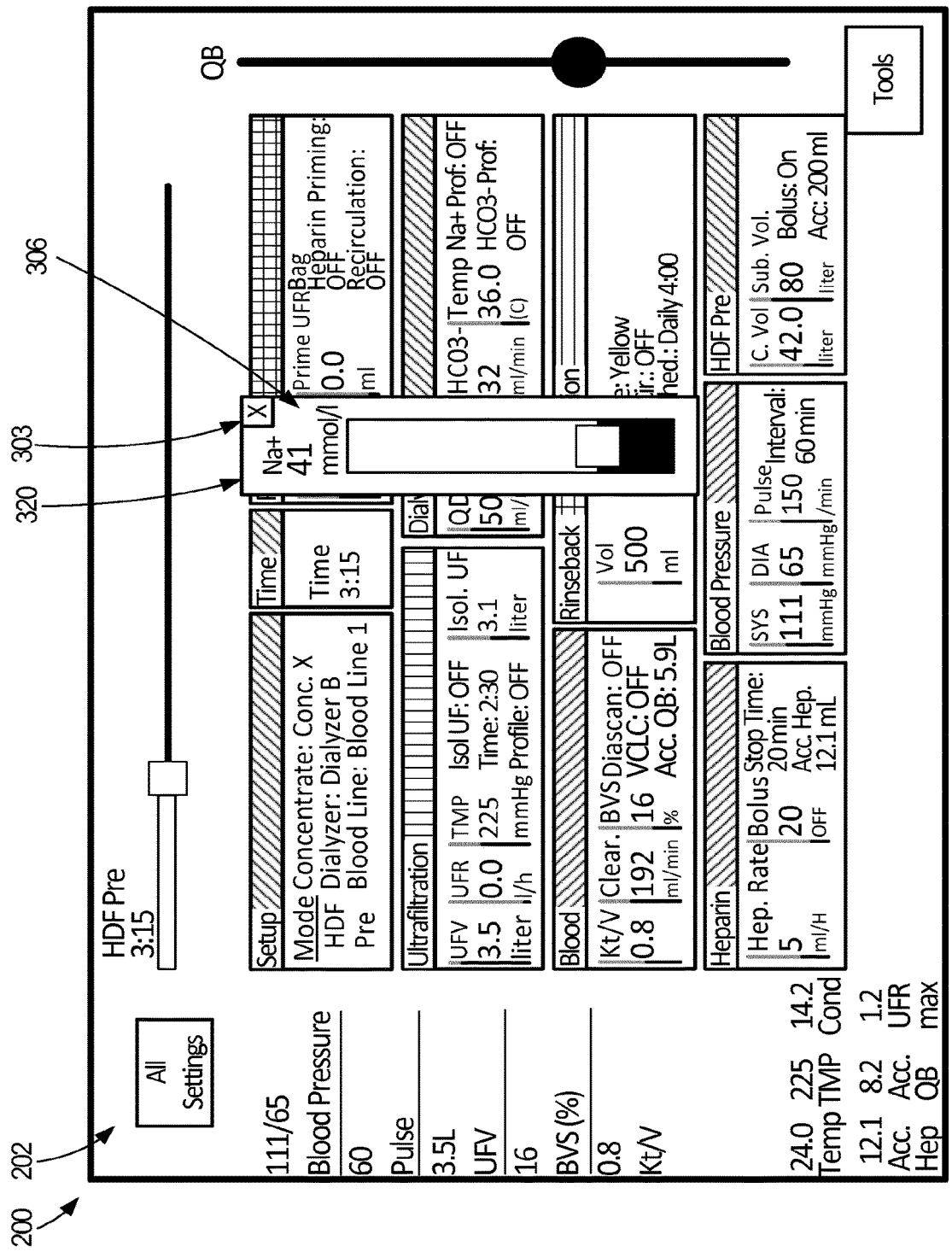
FIG. 10 depicts the graphical user interface of FIG. 5 including the plurality of mini settings cards and an exemplary single settings card portion of the "Dialysis Fluid" settings card corresponding to sodium concentration of dialysis/dialysate fluid.

In one or more exemplary embodiments, the user-interactable settings of the settings cards 300 may be adjusted without displaying or opening the corresponding settings card 300. For example, as shown in FIG. 10, a user-interactable setting may be adjusted directly from the mini settings cards 310. In one embodiment, user interaction of a user-interactable setting depicted on a mini settings card 310 may display a single setting card portion 320 of a settings card 300. For instance, a user may double-tap or tap-and-hold on a particular user-interactable setting of the mini settings card 310 to display a portion of the settings card 300 corresponding to the particular user-interactable setting. For instance, a user may have interacted with (e.g., double-tapped, tap-and-hold, etc.) the sodium concentration setting from the "Dialysis Fluid" mini settings card 310 of FIG. 5 to display the "Sodium Concentration" setting card portion 320 as shown in FIG. 10. With respect to the state diagram 50 of FIG. 3, the graphical user interface 200 may change from the mini settings card state 54 to the single setting card portion state 60 when a user interacts with a particular user-interactable setting of the mini settings card. To return to the mini settings card state 54, a user may select outside of single setting card portion 320 within the plurality of mini settings cards 310, or to return to the general graphical user interface state 52, a user may select outside of the plurality of mini settings cards 310 (and, e.g., not within a process feature graphical element 202). As shown in FIG. 10, the "Sodium Concentration" setting card portion 320 includes a bar-type parameter adjustment element 325 including a handle element 324 useable to adjust the sodium concentration of the dialysis/dialysate fluid. In one embodiment, user interaction of a user-interactable setting depicted on a mini settings card 310 may display a numerical key pad, which a user may use to enter, or modify, a parameter or setting. In one embodiment, user interaction of a user-interactable setting depicted on a mini settings card 310 may include moving a miniaturized slider (e.g., a miniaturized bar-type parameter adjustment element) on the mini settings card 310 to modify a parameter or setting.

Figure 11:
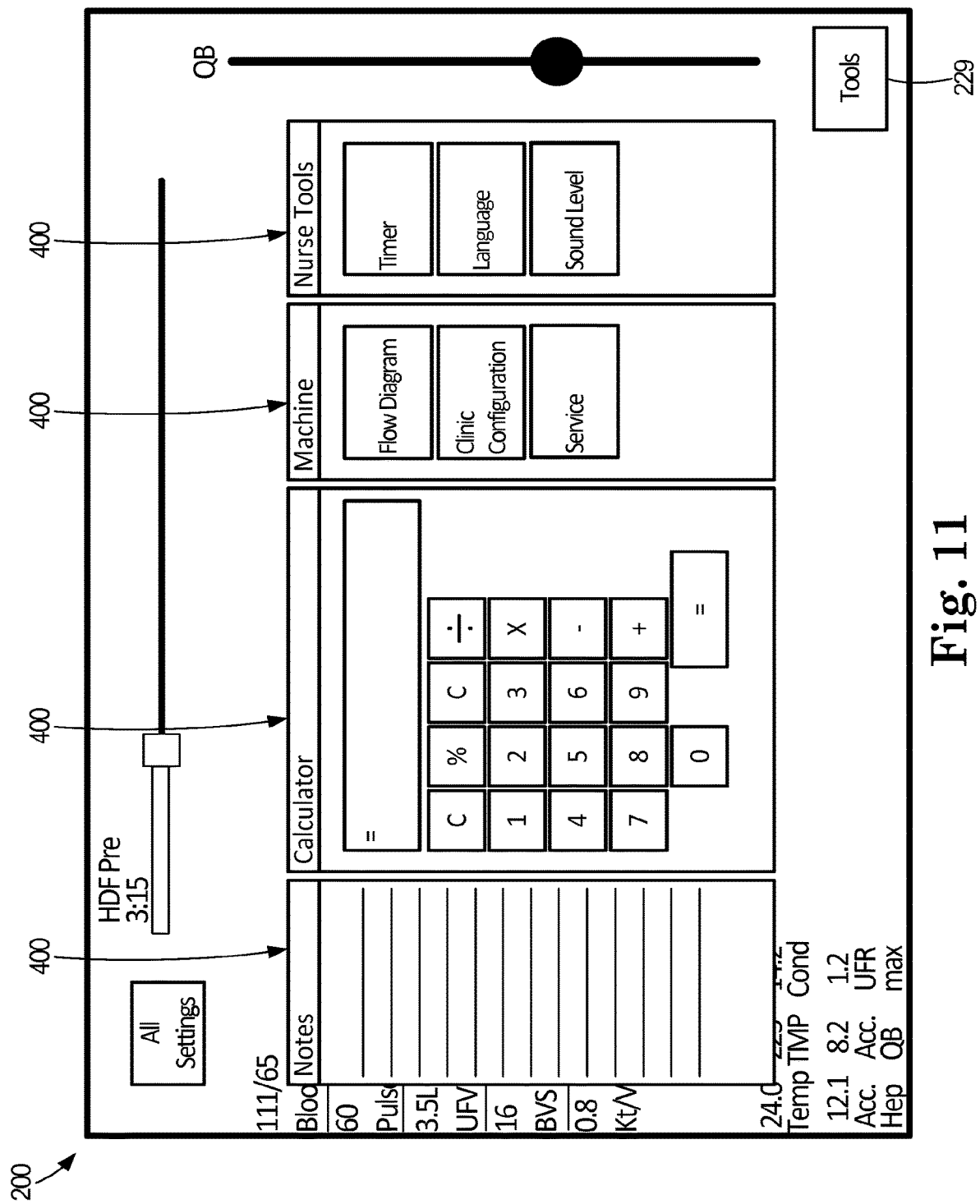
FIG. 11 depicts the graphical user interface of FIG. 4 including exemplary tools.

The exemplary graphical user interface 200 may further include tool cards 400 as shown in FIG. 11, which may be displayed in response to selection of a tools graphical element 229. The tool cards 400 do not correspond or relate to a treatment cycle and the one or more processes that occurs before, during, and after a blood treatment. Instead, the tool cards 400 may provide various tools to be used by a user that do not affect one or more settings within a treatment cycle. For example, a notes tool card 400 usable to take notes and a calculator tool card 400 usable as an on-screen calculator may be displayed as shown in FIG. 11. Further, a machine tool card 400 may be displayed that provides access to a flow diagram, a clinic configuration, and service menu, each of which may include various settings. However, the settings provided by the machine tool card 400 do not correspond or relate to a treatment cycle and the one or more processes that occurs before, during, and after a blood treatment. Instead, for example, the clinic configuration may include clinic-specific settings such as, for example, fixed alarm limits, feature on/off configuration, alarm buzzer volume, default modes, default consumables, etc. Still further, a nurse tools card may be displayed that provides access to a timer, language selection of the system, and a sound level adjustment of the system.

As described herein, the exemplary graphical user interface 200 may include a plurality of graphical regions, areas, and elements that include various settings and values related to the system, blood treatment apparatus, and blood treatments. Some graphical regions, areas, and elements may be displayed over the top of other graphical regions, areas, and elements obscuring the view and selection of the graphical regions, areas, and elements. For example, the plurality of mini settings cards 310 when displayed in FIG. 5 obscure the blood process feature graphical element 220, the dialysis fluid process feature graphical element 222, the ultrafiltration process feature graphical element 224, and the human process feature graphical element 226 of FIG. 4. However, for example, the plurality of mini settings cards 310 when displayed in FIG. 5 do not obscure other process feature graphical elements 202 such as, e.g., the blood flow process feature graphical element 228, the blood pressure process feature graphical element 211, the patient pulse process feature graphical element 212, the transmembrane pressure process feature graphical element 217, the treatment timeline process feature graphical element 260, etc.

The process feature graphical elements 202 that are obscured by the plurality of mini settings cards 310 in FIG. 5, as well as the settings cards 300 and single settings cards portions 320 in FIGS. 6-10, may be described as being located inside of a frame, or perimeter 199 as shown as a dashed line in FIGS. 12A-B. The region located inside the frame 199 may be defined as an inside region 190 and the region outside of the frame 199 may be defined as an outside region 192. Certain process feature graphical elements 202 may be selectively, or deliberately, located in the outside region 192 to avoid being obscured by the display of various graphical regions, areas, and elements such as the mini settings cards 310. Likewise, other process feature graphical elements 202 may be selectively, or deliberately, located in the inside region 190 to be obscured by the display of various graphical regions, areas, and elements such as the mini settings cards 310.

One or more settings cards 300 may be displayed, or depicted, on the graphical user interface 200 in response to one or more events of the extracorporeal blood treatment system (e.g., events that are not directly initiated by a user). One or more events, which trigger, or initiate, the display of one or more settings cards 300 may include one or more alarms, one or more timers (e.g., expiration of treatment time, etc.), and/or one or more user-performed tasks. For example, a single settings card 300 may be displayed automatically in response to, or based on, the occurrence of one or more events. For example, a "Treatment Time" settings card 300 may be displayed by itself on the graphical user interface 200 (similar to the "Blood Pressure" settings card 300 of FIG. 8) in response to expiration of the treatment time such that, e.g., a user may use the "Treatment Time" settings card to add time to the present treatment if desired.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the systems and methods described herein. Various modifications of the illustrative embodiments, as well as additional embodiments of the disclosure, will be apparent upon reference to this description.

What is claimed is:

1. An extracorporeal blood treatment system comprising:
   extracorporeal blood treatment apparatus comprising one or more pumps, one or more sensors, and one or more disposable elements for use in performing an extracorporeal blood treatment;
   a display apparatus comprising a graphical user interface, wherein the graphical user interface is configured to depict a plurality of settings cards and a plurality of mini settings cards; and
   a computing apparatus comprising one or more processors and operatively coupled to the extracorporeal blood treatment apparatus and the display apparatus, wherein the computing apparatus is configured to:
   provide the plurality of settings cards and the plurality of mini settings cards, wherein each settings card of the plurality of settings cards comprises one or more user-interactable settings related to one or more processes of the extracorporeal blood treatment system performable by the extracorporeal blood treatment apparatus, wherein each mini settings card of the plurality of mini settings cards is associated with a different settings card of the plurality of settings cards, wherein each mini settings card of the plurality of mini settings cards displays at least one of the one or more user-interactable settings of the associated settings card,
   display on the graphical user interface an all-settings graphical element and a plurality of process feature graphical elements, wherein the all-settings graphical element is associated with the display of the plurality of mini settings cards, wherein each process feature graphical element of the plurality of process feature graphical elements corresponds with a different process feature of the one or more processes performable by the extracorporeal blood treatment system using the extracorporeal blood treatment apparatus and is associated with the display of a single settings card of the plurality of settings cards, receive input from a user selecting the all-settings graphical element, display the plurality of mini settings cards at the same time on the graphical user interface such that all of the user-interactable settings for a treatment cycle of the plurality of settings cards are accessible by a user using the plurality of mini settings cards in response to selection of the all-settings graphical element, receive input from a user selecting a mini settings card of the plurality of displayed mini settings cards, display a settings card of the plurality of settings cards associated with the selected mini settings card in response to selection thereof, receive input from a user selecting a process feature graphical element of the plurality of process feature graphical elements, display a settings card of the plurality of settings cards associated with the selected process feature graphical element in response to selection thereof, receive input from the user using the one or more user-interactable settings of the displayed settings card to change one or more settings related to one or more processes of the extracorporeal blood treatment system performable by the extracorporeal blood treatment apparatus, change one or more settings related to one or more processes of the extracorporeal blood treatment system performable by the extracorporeal blood treatment apparatus in response to the received input from the user changing the one or more user-interactable settings of the displayed settings card, and perform an extracorporeal blood treatment using the extracorporeal blood treatment apparatus based on the changed one or more settings, wherein the plurality of settings cards define a card set, wherein the plurality of settings cards are further grouped into a plurality of card subsets, wherein each card subset comprises a plurality of settings cards that is less settings cards than the card set, wherein each settings card of the plurality of settings cards and the mini settings card of the plurality of mini settings cards associated therewith comprises a subset graphical indication to indicate which card subset of the plurality of card subsets the settings card and associated mini settings card belong to.

2. The system of claim 1, wherein the one or more user-interactable settings of the plurality of settings cards represent all of the user-interactable settings for a treatment cycle irrespective of the current phase of the treatment cycle.

3. The system of claim 1, wherein the computing apparatus is further configured to:

receive input from a user selecting a user-interactable setting of the one or more user-interactable settings of the displayed settings card;

display an auxiliary settings card portion comprising one or more additional user-interactable settings related to the selected user-interactable setting of the one or more user-interactable settings of the displayed settings card in response to selection thereof;

receive input from the user using the one or more additional user-interactable settings of the displayed auxiliary settings card portion; and change one or more settings related to one or more processes of the extracorporeal blood treatment system performable by the extracorporeal blood treatment apparatus in response to the received input from the user using the one or more additional user-interactable settings of the displayed auxiliary settings card portion.

4. The system of claim 1, wherein the subset graphical indication comprises a color theme, wherein one card subset of the plurality of card subsets is associated with blood, where the subset graphical indication for the card subset associated with blood is a red color theme.

5. The system of claim 1, wherein the plurality of settings cards are associated with a treatment cycle, wherein the computing apparatus is further configured to provide a plurality of system configuration settings cards defining a system configuration card set different from the plurality of settings cards associated with the treatment cycle including at least priming, treatment, and disinfection.

6. The system of claim 1, wherein, when the user selects one of the plurality of displayed mini settings cards to display the associated settings card, the associated settings cards displayed over the plurality of mini settings cards.

7. The system of claim 1, wherein, when the user selects one of the plurality of process feature graphical elements to display the associated settings card, the associated settings card is displayed without the plurality of mini settings cards being displayed.

8. The system of claim 7, wherein the displayed settings card associated with the selected process feature graphical element comprises:

an alphanumeric name identifying the process feature of the selected process feature graphical element; and an alphanumeric value depicting the value of a parameter associated with the process feature of the selected process feature graphical element.

9. The system of claim 1, wherein the computing apparatus is further configured to:

receive input from a user selecting an area of the graphical user interface outside of the plurality of displayed mini settings cards; and remove the plurality of displayed mini settings cards from being displayed on the graphical user interface in response to the selection of the area of the graphical user interface outside of the plurality of displayed mini settings cards.

10. The system of claim 1, wherein the computing apparatus is further configured to:

receive input from a user selecting an area of the graphical user interface outside of the displayed settings card; and remove the displayed settings card from being displayed on the graphical user interface in response to the selection of the area of the graphical user interface outside of the displayed settings card.

11. The system of claim 1, wherein the computing apparatus is further configured to:

receive input from a user using the at least one of the one or more user-interactable settings of one of the plurality of mini settings cards; and change one or more settings related to one or more processes of the extracorporeal blood treatment system performable by the extracorporeal blood treatment apparatus in response to the received user input from the user changing the at least one of the one or more user-interactable settings on one of the plurality of mini settings cards.

12. The system of claim 1, wherein the plurality of settings cards comprises a blood settings card, an ultrafiltration settings card, a dialysis fluid settings card, and a treatment time settings card.

13. The system of claim 1, wherein the plurality of settings cards comprises a disinfection settings card.

14. The system of claim 1, wherein the computing apparatus is further configured to display at least one settings card of the plurality of settings cards in response to a status change of one or more processes being performed.

15. The system of claim 1, wherein the plurality of mini settings cards comprises:
- a plurality of persistent mini settings cards configured to always be displayed; and
- one or more dependent mini settings cards configured to be displayed in response to at least one system configuration.

16. The system of claim 1, wherein each mini settings card of the plurality of mini settings cards is displayed in the same location of the graphical user interface when the plurality of mini settings cards are displayed.

17. The system of claim 1, wherein the display apparatus comprises a touchscreen.

18. An extracorporeal blood treatment system comprising:
- extracorporeal blood treatment apparatus comprising one or more pumps, one or more sensors, and one or more disposable elements for use in performing an extracorporeal blood treatment;
- a display apparatus comprising a graphical user interface, wherein the graphical user interface is configured to depict a plurality of settings cards and a plurality of mini settings cards; and
- a computing apparatus comprising one or more processors and operatively coupled to the extracorporeal blood treatment apparatus and the display apparatus, wherein the computing apparatus is configured to:
  - provide the plurality of settings cards and the plurality of mini settings cards, wherein each settings card of the plurality of settings cards comprises one or more user-interactable settings related to one or more processes of the extracorporeal blood treatment system performable by the extracorporeal blood treatment apparatus, wherein each mini settings card of the plurality of mini settings cards is associated with a different settings card of the plurality of settings cards, wherein each mini settings card of the plurality of mini settings cards displays at least one of the one or more user-interactable settings of the associated settings card,
  - display on the graphical user interface an all-settings graphical element and a plurality of process feature graphical elements, wherein the all-settings graphical element is associated with the display of the plurality of mini settings cards, wherein each process feature graphical element of the plurality of process feature graphical elements corresponds with a different process feature of the one or more processes performable by the extracorporeal blood treatment system using the extracorporeal blood treatment apparatus and is associated with the display of a single settings card of the plurality of settings cards,
  - receive input from a user selecting the all-settings graphical element,
  - display the plurality of mini settings cards at the same time on the graphical user interface such that all of the user-interactable settings for a treatment cycle of the plurality of settings cards are accessible by a user using the plurality of mini settings cards in response to selection of the all-settings graphical element,
  - receive input from a user selecting a mini settings card of the plurality of displayed mini settings cards,
  - display a settings card of the plurality of settings cards associated with the selected mini settings card in response to selection thereof,
  - receive input from a user selecting a process feature graphical element of the plurality of process feature graphical elements,
  - display a settings card of the plurality of settings cards associated with the selected process feature graphical element in response to selection thereof,
  - receive input from the user using the one or more user-interactable settings of the displayed settings card to change one or more settings related to one or more processes of the extracorporeal blood treatment system performable by the extracorporeal blood treatment apparatus,
  - change one or more settings related to one or more processes of the extracorporeal blood treatment system performable by the extracorporeal blood treatment apparatus in response to the received input from the user changing the one or more user-interactable settings of the displayed settings card, and
  - perform an extracorporeal blood treatment using the extracorporeal blood treatment apparatus based on the changed one or more settings,
  - wherein a plurality of user-interactable settings of the plurality of settings cards are associated with a prescription, wherein the plurality of user-interactable settings of the plurality of settings cards associated with the prescription are graphically identified in the plurality of settings cards and the mini settings cards.

19. An extracorporeal blood treatment system comprising:
- extracorporeal blood treatment apparatus comprising one or more pumps, one or more sensors, and one or more disposable elements for use in performing an extracorporeal blood treatment;
- a display apparatus comprising a graphical user interface, wherein the graphical user interface is configured to depict a plurality of settings cards and a plurality of mini settings cards; and
- a computing apparatus comprising one or more processors and operatively coupled to the extracorporeal blood treatment apparatus and the display apparatus, wherein the computing apparatus is configured to:
  - provide a plurality of settings cards and a plurality of mini settings cards, wherein each settings card of the plurality of settings cards comprises one or more user-interactable settings related to one or more processes of the extracorporeal blood treatment system performable by the extracorporeal blood treatment apparatus, wherein the one or more user-interactable settings of the plurality of settings cards represent all of the user-interactable settings for a treatment cycle irrespective of the current phase of the treatment cycle, wherein the treatment cycle includes at least preparation, treatment, and post-treatment phases, wherein each mini settings card of the plurality of mini settings cards is associated with a different settings card of the plurality of settings cards, wherein each mini settings card of the plurality of mini settings cards displays at least one of the one or more user-interactable settings of the associated settings card, display the plurality of mini settings cards at the same time on the graphical user interface such that all of the user-interactable settings for a treatment cycle of the plurality of settings cards are accessible by a user using the plurality of mini settings cards irrespective of the current phase of the treatment cycle, receive input from a user selecting a mini settings card of the plurality of displayed mini settings cards, display a settings card of the plurality of settings cards associated with the selected mini settings card in response to selection thereof, receive input from the user using the one or more user-interactable settings of the displayed settings card to change one or more settings related to one or more processes of the extracorporeal blood treatment system performable by the extracorporeal blood treatment apparatus, change one or more settings related to one or more processes of the extracorporeal blood treatment system performable by the extracorporeal blood treatment apparatus in response to the received input from the user using the one or more user-interactable settings of the displayed settings card; and performing an extracorporeal blood treatment using the extracorporeal blood treatment apparatus based on the changed one or more settings, wherein the plurality of settings cards defines a card set, wherein the plurality of settings cards is further grouped into a plurality of card subsets, wherein each card subset comprises a plurality of settings cards that is less settings cards than the card set, wherein each settings card of the plurality of settings cards and the mini settings card of the plurality of mini settings cards associated therewith comprises a subset graphical indication to indicate which card subset of the plurality of card subsets the settings card and associated mini settings card belong to.

20. The system of claim 19, wherein the subset graphical indication comprises a color theme, wherein one card subset of the plurality of card subsets is associated with blood, where the subset graphical indication for the card subset associated with blood is a red color theme.

21. An extracorporeal blood treatment system comprising:
extracorporeal blood treatment apparatus comprising one or more pumps, one or more sensors, and one or more disposable elements for use in performing an extracorporeal blood treatment;

a display apparatus comprising a graphical user interface, wherein the graphical user interface is configured to depict a plurality of settings cards and a plurality of mini settings cards; and a computing apparatus comprising one or more processors and operatively coupled to the extracorporeal blood treatment apparatus and the display apparatus, wherein the computing apparatus is configured to:

provide a plurality of settings cards and a plurality of mini settings cards, wherein each settings card of the plurality of settings cards comprises one or more user-interactable settings related to one or more processes of the extracorporeal blood treatment system performable by the extracorporeal blood treatment apparatus, wherein the one or more user-interactable settings of the plurality of settings cards represent all of the user-interactable settings for a treatment cycle irrespective of the current phase of the treatment cycle, wherein the treatment cycle includes at least preparation, treatment, and post-treatment phases, wherein each mini settings card of the plurality of mini settings cards is associated with a different settings card of the plurality of settings cards, wherein each mini settings card of the plurality of mini settings cards displays at least one of the one or more user-interactable settings of the associated settings card, display the plurality of mini settings cards at the same time on the graphical user interface such that all of the user-interactable settings for a treatment cycle of the plurality of settings cards are accessible by a user using the plurality of mini settings cards irrespective of the current phase of the treatment cycle, receive input from a user selecting a mini settings card of the plurality of displayed mini settings cards, display a settings card of the plurality of settings cards associated with the selected mini settings card in response to selection thereof, receive input from the user using the one or more user-interactable settings of the displayed settings card to change one or more settings related to one or more processes of the extracorporeal blood treatment system performable by the extracorporeal blood treatment apparatus, change one or more settings related to one or more processes of the extracorporeal blood treatment system performable by the extracorporeal blood treatment apparatus in response to the received input from the user using the one or more user-interactable settings of the displayed settings card; and performing an extracorporeal blood treatment using the extracorporeal blood treatment apparatus based on the changed one or more settings, wherein a plurality of user-interactable settings of the plurality of settings cards is associated with a prescription, wherein the plurality of user-interactable settings of the plurality of settings cards associated with the prescription is graphically identified in the plurality of settings cards and the mini settings cards.

22. The system of claim 21, wherein the computing apparatus is further configured to:
receive input from a user selecting a user-interactable setting of the one or more user-interactable settings of the displayed settings card;

display an auxiliary settings card portion comprising one or more additional user-interactable settings related to the selected user-interactable setting of the one or more user-interactable settings of the displayed settings card in response to selection thereof;

receive input from the user using the one or more additional user-interactable settings of the displayed auxiliary settings card portion; and change one or more settings related to one or more processes of the extracorporeal blood treatment system performable by the extracorporeal blood treatment apparatus in response to the received input from the user using the one or more additional user-interactable settings of the di splayed auxiliary settings card portion.

23. The system of claim 21, wherein the plurality of settings cards is associated with a treatment cycle, wherein the computing apparatus is further configured to provide a plurality of system configuration settings cards defining a system configuration card set different from the plurality of settings cards associated with the treatment cycle including at least priming, treatment, and disinfection.

24. The system of claim 21, wherein, when the user selects one of the plurality of displayed mini settings cards to display the associated settings card, the associated settings cards displayed over the plurality of mini settings cards.

25. The system of claim 21, wherein the computing apparatus is further configured to:
   receive input from a user selecting an area of the graphical user interface outside of the plurality of displayed mini settings cards; and
   remove the plurality of displayed mini settings cards from being displayed on the graphical user interface in response to the selection of the area of the graphical user interface outside of the plurality of displayed mini settings cards.

26. The system of claim 21, wherein the computing apparatus is further configured to:
   receive input from a user selecting an area of the graphical user interface outside of the displayed settings card; and
   remove the displayed settings card from being displayed on the graphical user interface in response to the selection of the area of the graphical user interface outside of the displayed settings card.

27. The system of claim 21, wherein the computing apparatus is further configured to:
   receive input from the user using the at least one of the one or more user-interactable settings on one of the plurality of mini settings cards; and
   change one or more settings related to one or more processes of the extracorporeal blood treatment system performable by the extracorporeal blood treatment apparatus in response to the received input from the user changing the at least one of the one or more user-interactable settings on one of the plurality of mini settings cards.

28. The system of claim 21, wherein the computing apparatus is further configured to display at least one settings card of the plurality of settings cards in response to a status change of one or more processes being performed.

29. The system of claim 21, wherein the plurality of mini settings cards comprises:
   a plurality of persistent mini settings cards configured to always be displayed; and
   one or more dependent mini settings cards configured to be displayed in response to at least one system configuration.

30. The system of claim 21, wherein each mini settings card of the plurality of mini settings cards is displayed in the same location of the graphical user interface when the plurality of mini settings cards is displayed.

* * * * *